United States Patent
Kumar et al.

(10) Patent No.: US 11,109,941 B2
(45) Date of Patent: Sep. 7, 2021

(54) TRACKING SURGICAL ITEMS WITH PREDICTION OF DUPLICATE IMAGING OF ITEMS

(71) Applicant: Gauss Surgical, Inc., Menlo Park, CA (US)

(72) Inventors: Mayank Kumar, Sunnyvale, CA (US); Kevin J. Miller, Mountain View, CA (US); Siddarth Satish, Redwood City, CA (US)

(73) Assignee: Gauss Surgical, Inc., Menlo Park, CA (US)

( * ) Notice: Subject to any disclaimer, the term of this patent is extended or adjusted under 35 U.S.C. 154(b) by 31 days.

(21) Appl. No.: 16/459,418

(22) Filed: Jul. 1, 2019

(65) Prior Publication Data
US 2019/0388182 A1    Dec. 26, 2019

Related U.S. Application Data

(63) Continuation of application No. PCT/US2017/068234, filed on Dec. 22, 2017.
(Continued)

(51) Int. Cl.
*A61B 90/96* (2016.01)
*A61B 90/92* (2016.01)
(Continued)

(52) U.S. Cl.
CPC .............. *A61B 90/96* (2016.02); *A61B 90/92* (2016.02); *G06K 9/4671* (2013.01);
(Continued)

(58) Field of Classification Search
CPC ......... A61B 34/20; A61B 50/37; A61B 90/92; A61B 90/96; G06K 9/4671; G06K 9/6211;
(Continued)

(56) References Cited

U.S. PATENT DOCUMENTS

| 2,707,955 A | 5/1955 | Borden |
| 3,182,252 A | 5/1965 | van den Berg |

(Continued)

FOREIGN PATENT DOCUMENTS

| CA | 2870635 A1 | 10/2013 |
| CN | 101505813 A | 8/2009 |
| JP | S-59-161801 U | 10/1984 |
| JP | S-61-176357 A | 8/1986 |
| JP | S-62-144652 A | 6/1987 |
| JP | H-06-510210 A | 11/1994 |
| JP | H-07-308312 A | 11/1995 |
| JP | H-11-37845 A | 2/1999 |

(Continued)

OTHER PUBLICATIONS

"European Application Serial No. 17887131.5, Extended European Search Report dated Jul. 16, 2020", 8 pgs.
(Continued)

*Primary Examiner* — Manuchehr Rahmjoo
(74) *Attorney, Agent, or Firm* — Schwegman Lundberg & Woessner, P.A.

(57) ABSTRACT

A computer-implemented method for tracking surgical textiles includes receiving a first image comprising a first textile-depicting image region, receiving a second image comprising a second textile-depicting image region, measuring a likelihood that the first and second image regions depict at least a portion of the same textile, and incrementing an index counter if the measure of likelihood does not meet a predetermined threshold. The measure of likelihood may be based on at least one classification feature at least partially based on aspects or other features of the first and second images.

28 Claims, 13 Drawing Sheets

Related U.S. Application Data

(60) Provisional application No. 62/441,494, filed on Jan. 2, 2017.

(51) Int. Cl.
| | | |
|---|---|---|
| *G06T 7/33* | (2017.01) | |
| *G06K 9/46* | (2006.01) | |
| *G06K 9/62* | (2006.01) | |
| *A61B 34/20* | (2016.01) | |
| *A61B 50/37* | (2016.01) | |

(52) U.S. Cl.
CPC ............ *G06K 9/6211* (2013.01); *G06T 7/337* (2017.01); *A61B 34/20* (2016.02); *A61B 50/37* (2016.02); *G06T 2207/20164* (2013.01)

(58) Field of Classification Search
CPC . G06T 2207/10016; G06T 2207/10024; G06T 2207/10028; G06T 2207/20021; G06T 2207/20061; G06T 2207/20076; G06T 2207/20081; G06T 2207/20084; G06T 2207/20164; G06T 2207/30124; G06T 2207/30204; G06T 7/0014; G06T 7/0016; G06T 7/33; G06T 7/337; G06T 7/62
See application file for complete search history.

(56) References Cited

U.S. PATENT DOCUMENTS

| | | |
|---|---|---|
| 3,199,507 A | 8/1965 | Kamm |
| 3,367,431 A | 2/1968 | Prindle Baker |
| 3,646,938 A | 3/1972 | Haswell |
| 3,832,135 A | 8/1974 | Drozdowski et al. |
| 3,864,571 A | 2/1975 | Stillman et al. |
| 3,948,390 A | 4/1976 | Ferreri |
| 4,105,019 A | 8/1978 | Haswell |
| 4,149,537 A | 4/1979 | Haswell |
| 4,244,369 A | 1/1981 | McAvinn et al. |
| 4,402,373 A | 9/1983 | Comeau |
| 4,422,548 A | 12/1983 | Cheesman et al. |
| 4,429,789 A | 2/1984 | Puckett |
| 4,562,842 A | 1/1986 | Morfeld et al. |
| 4,583,546 A | 4/1986 | Garde |
| 4,642,089 A | 2/1987 | Zupkas et al. |
| 4,681,571 A | 7/1987 | Nehring |
| 4,773,423 A | 9/1988 | Hakky |
| 4,784,267 A | 11/1988 | Gessler et al. |
| 4,832,198 A | 5/1989 | Alikhan |
| 4,917,694 A | 4/1990 | Jessup |
| 4,922,922 A | 5/1990 | Pollock et al. |
| 5,029,584 A | 7/1991 | Smith |
| 5,031,642 A | 7/1991 | Nosek |
| 5,048,683 A | 9/1991 | Westlake |
| 5,119,814 A | 6/1992 | Minnich |
| 5,132,087 A | 7/1992 | Manion et al. |
| 5,190,059 A | 3/1993 | Fabian et al. |
| 5,231,032 A | 7/1993 | Ludvigsen |
| 5,236,664 A | 8/1993 | Ludvigsen |
| 5,285,682 A | 2/1994 | Micklish |
| 5,348,533 A | 9/1994 | Papillon et al. |
| 5,369,713 A | 11/1994 | Schwartz et al. |
| 5,492,537 A | 2/1996 | Vancaillie |
| 5,522,805 A | 6/1996 | Vancaillie et al. |
| 5,629,498 A | 5/1997 | Pollock et al. |
| 5,633,166 A | 5/1997 | Westgard et al. |
| 5,650,596 A | 7/1997 | Morris et al. |
| 5,709,670 A | 1/1998 | Vancaillie et al. |
| 5,807,358 A | 9/1998 | Herweck et al. |
| 5,851,835 A | 12/1998 | Groner |
| 5,923,001 A | 7/1999 | Morris et al. |
| 5,931,824 A | 8/1999 | Stewart et al. |
| 5,944,668 A | 8/1999 | Vancaillie et al. |
| 5,956,130 A | 9/1999 | Vancaillie et al. |
| 5,984,893 A | 11/1999 | Ward |
| 5,996,889 A | 12/1999 | Fuchs et al. |
| 6,006,119 A | 12/1999 | Soller et al. |
| 6,061,583 A | 5/2000 | Ishihara et al. |
| 6,359,683 B1 | 3/2002 | Berndt |
| 6,510,330 B1 | 1/2003 | Enejder |
| 6,641,039 B2 | 11/2003 | Southard |
| 6,699,231 B1 | 3/2004 | Sterman et al. |
| 6,730,054 B2 | 5/2004 | Pierce et al. |
| 6,777,623 B2 | 8/2004 | Ballard |
| 6,998,541 B2 | 2/2006 | Morris et al. |
| 7,001,366 B2 | 2/2006 | Ballard |
| 7,112,273 B2 | 9/2006 | Weigel et al. |
| 7,147,626 B2 | 12/2006 | Goodman et al. |
| 7,158,030 B2 | 1/2007 | Chung |
| 7,180,014 B2 | 2/2007 | Farber et al. |
| 7,274,947 B2 | 9/2007 | Koo et al. |
| 7,297,834 B1 | 11/2007 | Shapiro |
| 7,299,981 B2 | 11/2007 | Hickle et al. |
| 7,384,399 B2 | 6/2008 | Ghajar |
| 7,430,047 B2 | 9/2008 | Budd et al. |
| 7,430,478 B2 | 9/2008 | Fletcher-Haynes et al. |
| 7,469,727 B2 | 12/2008 | Marshall |
| 7,499,581 B2 | 3/2009 | Tribble et al. |
| 7,557,710 B2 | 7/2009 | Sanchez et al. |
| 7,641,612 B1 | 1/2010 | McCall |
| D611,731 S | 3/2010 | Levine |
| 7,670,289 B1 | 3/2010 | McCall |
| 7,703,674 B2 | 4/2010 | Stewart |
| 7,708,700 B2 | 5/2010 | Ghajar |
| 7,711,403 B2 | 5/2010 | Jay et al. |
| 7,749,217 B2 | 7/2010 | Podhajsky |
| 7,795,491 B2 | 9/2010 | Stewart et al. |
| 7,804,982 B2 | 9/2010 | Howard et al. |
| 7,819,818 B2 | 10/2010 | Ghajar |
| 7,909,806 B2 | 3/2011 | Goodman et al. |
| 7,966,269 B2 | 6/2011 | Bauer et al. |
| 7,995,816 B2 | 8/2011 | Roger et al. |
| 8,025,173 B2 | 9/2011 | Michaels |
| 8,105,296 B2 | 1/2012 | Morris et al. |
| 8,181,860 B2 | 5/2012 | Fleck et al. |
| 8,241,238 B2 | 8/2012 | Hiruma et al. |
| 8,279,068 B2 | 10/2012 | Morris et al. |
| 8,398,546 B2 | 3/2013 | Pacione et al. |
| 8,472,693 B2 | 6/2013 | Davis et al. |
| 8,479,989 B2 | 7/2013 | Fleck et al. |
| 8,576,076 B2 | 11/2013 | Morris et al. |
| 8,626,268 B2 | 1/2014 | Adler et al. |
| 8,693,753 B2 | 4/2014 | Nakamura |
| 8,704,178 B1 | 4/2014 | Pollock et al. |
| 8,792,693 B2 | 7/2014 | Satish et al. |
| 8,897,523 B2 | 11/2014 | Satish et al. |
| 8,983,167 B2 | 3/2015 | Satish et al. |
| 9,171,368 B2 | 10/2015 | Satish et al. |
| 9,595,104 B2 | 3/2017 | Satish et al. |
| 9,652,655 B2 | 5/2017 | Satish et al. |
| 9,824,441 B2 | 11/2017 | Satish et al. |
| 9,936,906 B2 | 4/2018 | Satish et al. |
| 10,282,839 B2 | 5/2019 | Satish et al. |
| 2003/0095197 A1 | 5/2003 | Wheeler et al. |
| 2003/0130596 A1 | 7/2003 | Von Der Goltz |
| 2004/0031626 A1 | 2/2004 | Morris et al. |
| 2004/0129678 A1 | 7/2004 | Crowley et al. |
| 2005/0051466 A1 | 3/2005 | Carter et al. |
| 2005/0163354 A1 | 7/2005 | Ziegler |
| 2005/0265996 A1 | 12/2005 | Lentz |
| 2006/0058593 A1 | 3/2006 | Drinan et al. |
| 2006/0178578 A1 | 8/2006 | Tribble et al. |
| 2006/0224086 A1 | 10/2006 | Harty |
| 2007/0004959 A1 | 1/2007 | Carrier et al. |
| 2007/0108129 A1 | 5/2007 | Mori et al. |
| 2007/0243137 A1 | 10/2007 | Hainfeld |
| 2007/0287182 A1 | 12/2007 | Morris et al. |
| 2008/0029416 A1 | 2/2008 | Paxton |
| 2008/0030303 A1 | 2/2008 | Kobren et al. |
| 2008/0045845 A1 | 2/2008 | Pfeiffer et al. |
| 2008/0194906 A1 | 8/2008 | Mahony et al. |
| 2009/0076470 A1 | 3/2009 | Ryan |
| 2009/0317002 A1 | 12/2009 | Dein |
| 2010/0003714 A1 | 1/2010 | Bachur |

(56) References Cited

U.S. PATENT DOCUMENTS

| | | |
|---|---|---|
| 2010/0007727 A1 | 1/2010 | Torre-Bueno |
| 2010/0025336 A1 | 2/2010 | Carter et al. |
| 2010/0027868 A1 | 2/2010 | Kosaka et al. |
| 2010/0066996 A1 | 3/2010 | Kosaka et al. |
| 2010/0087770 A1 | 4/2010 | Bock |
| 2010/0150759 A1 | 6/2010 | Mazur et al. |
| 2010/0280117 A1 | 11/2010 | Patrick et al. |
| 2011/0066182 A1 | 3/2011 | Falus |
| 2011/0118647 A1 | 5/2011 | Paolini et al. |
| 2011/0192745 A1 | 8/2011 | Min |
| 2011/0196321 A1 | 8/2011 | Wudyka |
| 2011/0200239 A1 | 8/2011 | Levine et al. |
| 2011/0275957 A1 | 11/2011 | Bhandari |
| 2011/0305376 A1 | 12/2011 | Neff |
| 2011/0316973 A1 | 12/2011 | Miller et al. |
| 2012/0000297 A1 | 1/2012 | Hashizume et al. |
| 2012/0064132 A1 | 3/2012 | Aizawa et al. |
| 2012/0065482 A1 | 3/2012 | Robinson et al. |
| 2012/0127290 A1 | 5/2012 | Tojo et al. |
| 2012/0210778 A1 | 8/2012 | Palmer et al. |
| 2012/0257188 A1 | 10/2012 | Yan et al. |
| 2012/0262704 A1 | 10/2012 | Zahniser et al. |
| 2012/0262705 A1 | 10/2012 | Zahniser et al. |
| 2012/0309636 A1 | 12/2012 | Gibbons et al. |
| 2012/0327365 A1 | 12/2012 | Makihira |
| 2013/0088354 A1 | 4/2013 | Thomas |
| 2013/0094996 A1 | 4/2013 | Janssenswillen |
| 2013/0170729 A1 | 7/2013 | Wardlaw et al. |
| 2013/0308852 A1 | 11/2013 | Hamsici et al. |
| 2013/0308861 A1 | 11/2013 | Cordara et al. |
| 2014/0079297 A1 | 3/2014 | Tadayon et al. |
| 2014/0207091 A1 | 7/2014 | Heagle et al. |
| 2014/0330094 A1 | 11/2014 | Pacione et al. |
| 2016/0074128 A1 | 3/2016 | Dein |
| 2017/0186160 A1 | 6/2017 | Satish et al. |
| 2017/0352152 A1 | 12/2017 | Satish et al. |
| 2019/0008427 A1 | 1/2019 | Satish et al. |

FOREIGN PATENT DOCUMENTS

| | | | |
|---|---|---|---|
| JP | 2000-227390 A | 8/2000 | |
| JP | 2002-331031 A | 11/2002 | |
| JP | 2003-075436 A | 3/2003 | |
| JP | 2005-052288 A | 3/2005 | |
| JP | 3701031 B2 | 9/2005 | |
| JP | 2006-280445 A | 10/2006 | |
| JP | 2008-055142 A | 3/2008 | |
| JP | 2008-519604 A | 6/2008 | |
| JP | 2010-516429 A | 5/2010 | |
| JP | 2011-036371 A | 2/2011 | |
| JP | 2011-515681 A | 5/2011 | |
| JP | 2011-252804 A | 12/2011 | |
| WO | WO-92/17787 A1 | 10/1992 | |
| WO | WO-1996/039927 A1 | 12/1996 | |
| WO | WO-2006/053208 A1 | 5/2006 | |
| WO | WO-2008/094703 A2 | 8/2008 | |
| WO | WO-2009/117652 A1 | 9/2009 | |
| WO | WO-2011/019576 A1 | 2/2011 | |
| WO | WO-2011/145351 A1 | 11/2011 | |
| WO | WO-2013/009709 A2 | 1/2013 | |
| WO | WO-2013/172874 A1 | 11/2013 | |
| WO | WO-2013/173356 A1 | 11/2013 | |
| WO | WO-2016133767 A1 | 8/2016 | |
| WO | WO-2018125812 A1 | 7/2018 | |

OTHER PUBLICATIONS

Garcia-Martinez, Alvaro, et al., "Automatic detection of surgical gauzes using Computer Vision", 23rd Mediterranean Conference on Control and Automation (MED), IEEE, (Jun. 16, 2015), 747-751.
"International Application Serial No. PCT/US2017/068234, International Preliminary Report on Patentability dated Jul. 11, 2019", 11 pgs.
"European Application Serial No. 17887131.5, Response to Communication pursuant to Rules 161(2) and 162 EPC filed Feb. 13, 2020", 10 pgs.
ACOG (2012). "Optimizing protocols in obstetrics," Series 2, 25 total pages.
Adkins, A.R. et al. (2014). "Accuracy of blood loss estimations among anesthesia providers," AANA Journal 82(4):300-306.
Aklilu, A. Gauss Surgical Measures Blood Loss with a Smartphone. Jun. 14, 2012. <http://www.health2con.com/news/2012/06/14/gauss-surgical-measures-blood-loss-with-a-smartphone/>, 2 pages.
Al-Kadri, H.M. et al. (2014). "Effect of education and clinical assessment on the accuracy of post partum blood loss estimation," BMC Preg. Childbirth 14:110, 7 total pages.
AWHONN Practice Brief (2014). "Quantification of blood loss: AWHONN practice brief number 1," AWHONN p. 1-3.
Bellad, M.B. et al. (2009). "Standardized Visual Estimation of Blood Loss during Vaginal Delivery with Its Correlation Hematocrit Changes—A Descriptive Study." South Asian Federation of Gynecology 1:29-34.
Bose, P. et al. (2006). "Improving the accuracy of estimated blood loss at obstetric haemorrhage using clinical reconstructions," BJOG 113(8):919-924.
Eipe, N. et al. (2006). "Perioperative blood loss assessment—How accurate?" Indian J. Anaesth. 50(1):35-38.
Extended European Search Report dated Apr. 1, 2015, for EP Application No. 12 810 640.8, filed on Jul. 9, 2012, 8 pages.
Extended European Search Report dated Nov. 23, 2015, for EP Application No. 13 790 688.9, filed on May 14, 2013, 9 pages.
Extended European Search Report dated Nov. 17, 2015, for EP Application No. 13 790 449.6, filed on Jan. 10, 2013, 8 pages.
Extended European Search Report dated Nov. 4, 2016, for EP Application No. 16 183 350.4, filed on Jul. 9, 2012, 9 pages.
Extended European Search Report dated Jul. 12, 2019, for EP Application No. 19 156 549.8, filed on Jul. 9, 2012, 8 pages.
Final Office Action dated Feb. 12, 2016, for U.S. Appl. No. 13/544,664, filed Jul. 9, 2012, 9 pages.
Final Office Action dated Aug. 26, 2016, for U.S. Appl. No. 13/894,054, filed May 14, 2013, 7 pages.
Final Office Action dated Jul. 26, 2016, for U.S. Appl. No. 14/876,628, filed Oct. 6, 2015, 5 pages.
Habak, P.J. et al. (2016). "A comparison of visual estimate versus calculated estimate of blood loss at vaginal delivery," British J. Med. Medical Res. 11(4):1-7.
Holmes, A.A. et al. (2014). "Clinical evaluation of a novel system for monitoring surgical hemoglobin loss," Anesth. Analg. 119(3):588-594.
International Search Report dated Sep. 17, 2012, for PCT Application No. PCT/US2012/045969, filed on Jul. 9, 2012, 2 pages.
International Search Report dated Sep. 24, 2013, for PCT Application No. PCT/US2013/040976, filed on May 14, 2013, 2 pages.
International Search Report dated Mar. 26, 2013, for PCT Application No. PCT/US2013/021075, filed on Jan. 10, 2013, 2 pages.
International Search Report dated Feb. 26, 2018, for PCT Application No. PCT/US2017/068234, filed on Dec. 22, 2017, 2 pages.
Jones, R. (2015). "Quantitative measurement of blood loss during delivery," AWHONN p. S41.
Kamiyoshihara, M. et al. The Utility of an Autologous Blood Salvage System in Emergency Thoracotomy for a Hemothorax After Chest Trauma. Gen. Thorac. Cardiovasc. Surg. (2008); vol. 56, p. 222.
Lyndon, A. et al. (2010). "Blood loss: Clinical techniques for ongoing quantitative measurement," CMQCC Obstetric Hemorrhage Toolkit, pp. 1-7.
Lyndon, A. et al. (2015). "Cumulative quantitative assessment of blood loss," CMQCC Obstetric Hemorrhage Toolkit Version 2.0, pp. 80-85.
Manikandan, D. et al. (2015). "Measurement of blood loss during adenotonsillectomy in children and factors affecting it," Case Reports in Clinical Medicine 4:151-156.
Merck for Mother's Program (2012). Blood loss measurement: Technology opportunity assessment, 9 total pages.
Non-Final Office Action dated Aug. 13, 2015, for U.S. Application No. 13/544,664, filed Jul. 9, 2012, 8 pages.

(56) References Cited

OTHER PUBLICATIONS

Non-Final Office Action dated Aug. 2, 2016, for U.S. Appl. No. 13/544,664, filed Jul. 9, 2012, 6 pages.
Non-Final Office Action dated May 9, 2014, for U.S. Appl. No. 13/544,679, filed Jul. 9, 2012, 7 pages.
Non-Final Office Action dated Mar. 30, 2016, for U.S. Appl. No. 13/894,054, filed May 14, 2013, 9 pages.
Non-Final Office Action dated Sep. 5, 2014, for U.S. Appl. No. 13/738,919, filed Jan. 10, 2013, 8 pages.
Non-Final Office Action dated Mar. 20, 2015, for U.S. Appl. No. 14/613,807, filed Feb. 4, 2015, 8 pages.
Non-Final Office Action dated Dec. 15, 2015, for U.S. Appl. No. 14/876,628, filed Oct. 6, 2015, 8 pages.
Non-Final Office Action dated Apr. 20, 2017, for U.S. Appl. No. 13/894,054, filed May 14, 2013, 7 pages.
Non-Final Office Action dated Apr. 11, 2018, for U.S. Appl. No. 15/416,986, filed Jan. 26, 2017, 6 pages.
Non-Final Office Action dated Feb. 21, 2019, for U.S. Appl. No. 15/594,017, filed May 12, 2017, 23 pages.
Notice of Allowance dated May 12, 2014, for U.S. Appl. No. 13/544,646, filed Jul. 9, 2012, 10 pages.
Notice of Allowance dated Sep. 3, 2014, for U.S. Appl. No. 13/544,679, filed Jul. 9, 2012, 8 pages.
Notice of Allowance dated Nov. 10, 2014, for U.S. Appl. No. 13/738,919, filed Jan. 10, 2013, 10 pages.
Notice of Allowance dated Jun. 25, 2015, for U.S. Appl. No. 14/613,807, filed Feb. 4, 2015, 10 pages.
Notice of Allowance dated Oct. 26, 2016, for U.S. Appl. No. 14/876,628, filed Oct. 6, 2015, 11 pages.
Notice of Allowance dated Feb. 15, 2017, for U.S. Appl. No. 13/544,664, filed Jul. 9, 2012, 10 pages.
Notice of Allowance dated Nov. 20, 2017, for U.S. Appl. No. 13/894,054, filed May 14, 2013, 8 pages.
Notice of Allowance dated Jan. 24, 2019, for U.S. Appl. No. 15/416,986, filed Jan. 26, 2017, 9 pages.
Pogorelc, D. "iPads in the OR: New Mobile Platform to Monitor Blood Loss During Surgery". MedCityNews, Jun. 6, 2012. [retrieved from the internet Mar. 11, 2014] <http://medcitynews.com/2012/06/ipads-in-the-or-new-mobile-platform-to-monitor-blood-loss-during-surgery>, 4 pages.
Roston, A.B. et al. (2012). "Chapter 9: Blood loss: Accuracy of visual estimation," in *A comprehensive textbook of postpartum hemorrhage: An essential clinical reference for effective management*, 2$^{nd}$ edition, Sapiens publishing, pp. 71-72.
Sant et al. (2012). "Exsanguinated Blood Volume Estimation Using Fractal Analysis of Digital Images," *Journal of Forensic Sciences* 57:610-617.
Schorn, M.N. (2010). "Measurement of blood loss: Review of the literature," *J. Midwifery and Women's Health* 55(1):20-27.
Sukprasert, M. et al. (2006). "Increase accuracy of visual estimation of blood loss from education programme," *J. Med. Assoc. Thai* 89(suppl. 4):554-559.
Written Opinion of the International Searching Authority dated Sep. 17, 2012, for PCT Application No. PCT/US2012/045969, filed on Jul. 9, 2012, 4 pages.
Written Opinion of the International Searching Authority dated Sep. 24, 2013, for PCT Application No. PCT/US2013/040976, filed on May 14, 2013, 4 pages.
Written Opinion of the International Searching Authority dated Mar. 26, 2013, for PCT Application No. PCT/US2013/021075, filed on Jan. 10, 2013, 6 pages.
Written Opinion of the International Searching Authority dated Feb. 26, 2018, for PCT Application No. PCT/US2017/068234, filed on Dec. 22, 2017, 9 pages.
U.S. Appl. No. 16/392,345, filed Apr. 23, 2019, by Satish et al. (Copy not attached).

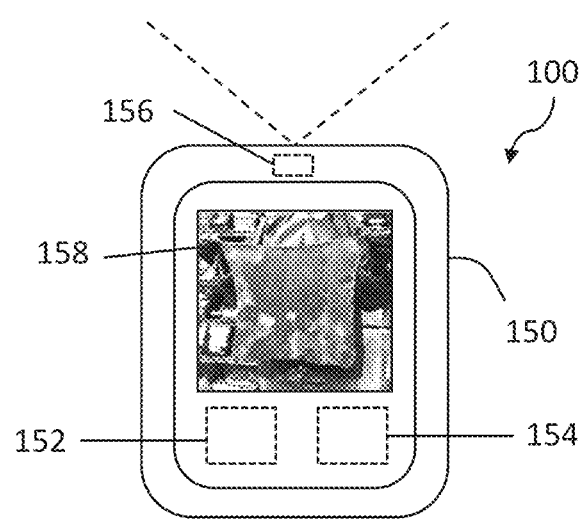
FIG. 1

| Classification Feature | Description |
|---|---|
| distanceFeatures | Distance between the feature descriptors in the descriptor space |
| goodnessHomography | Goodness of fit for the homography model mapping between first and second images |
| angleHough | Consensus voting ratio for angle of rotation |
| measureMatches | Measure of matching keypoints between the first and second images |
| scaleFeatures | Consistency in the scale of the feature descriptors between the first and second images |
| fluidRegionRatio | Ratio of the area of the fluid region to the total textile area in the image |
| fluidEstimate | Estimate of fluid component present in the image |

FIG. 5

| Dataset | Classifier | True positive | False positive | F Score |
|---|---|---|---|---|
| Set 0 | RF, n_est = 50 | 0.80 | 0.17 | 0.813 |
| | RF, n_est = 25 | 0.82 | 0.19 | 0.814 |
| | KNN, K = 20 | 0.84 | 0.25 | 0.801 |
| Set 1 | RF, n_est = 50 | 0.83 | 0.13 | 0.847 |
| | SVC, kernel ='rbf' | 0.80 | 0.13 | 0.826 |
| | KNN, K = 20 | 0.82 | 0.16 | 0.832 |
| Set 2 | RF, n_est = 200 | 0.93 | 0.17 | 0.886 |
| | ET, n_est = 100 | 0.89 | 0.10 | 0.893 |
| | KNN, K = 20 | 0.84 | 0.07 | 0.870 |
| Set 3 | RF, n_est = 50 | 0.94 | 0.03 | 0.953 |
| | ET, n_est = 100 | 0.94 | 0.02 | 0.957 |
| | KNN, K = 20 | 0.97 | 0.05 | 0.958 |

FIG. 10

TRACKING SURGICAL ITEMS WITH PREDICTION OF DUPLICATE IMAGING OF ITEMS

CROSS-REFERENCE TO RELATED APPLICATIONS

This application is a continuation of International Patent Application No. PCT/US2017/068234, filed on Dec. 22, 2017, which claims priority to U.S. Patent Application Ser. No. 62/441,494, filed on Jan. 2, 2017, all of which are hereby incorporated by reference in their entireties.

TECHNICAL FIELD

This invention relates generally to the field of surgical item tracking, and more specifically to new and useful systems and methods for tracking surgical items with prediction of duplicate imaging of items.

BACKGROUND

Surgical textiles (e.g., sponges, towels, etc.) are typically used during a surgical procedure to absorb loss of patient fluids, such as blood. For example, one or more surgical textiles may be placed inside the patient at a surgical site to absorb blood, and subsequently removed (e.g., upon saturation or after the procedure is complete). However, there is a risk that at least some of the surgical textiles may be inadvertently retained inside the patient. Retained foreign objects such as textiles may harm patient health such as by causing infection or even death, and may require additional surgeries or hospital readmission in order to remove the retained object.

One traditional approach to avoid inadvertent retention of surgical textiles is based on a manual count before and after the surgical procedure. For example, medical staff may perform manual counts of number of surgical textiles before their use (e.g., upon opening a new sterile package of surgical textiles) and after their use (e.g., upon removal from the patient's surgical site). A discrepancy between the manual counts may prompt medical stall to locate any apparently missing textiles, perform a recount, perform an X-ray scan of the patient, or perform other risk mitigation. However, human error in such manual counting introduces uncertainty in whether the counts are correct, thereby potentially causing medical staff to incorrectly conclude that there is a retained surgical textile, or worse, incorrectly conclude that all surgical textiles are accounted for and that all textiles are removed from the patient.

Another conventional approach to identify retained surgical textiles in a patient is to use specialized surgical textiles having tags (e.g., RFID, bar codes, etc.) that are scannable during the "before" and "after" counts to help improve accuracy in the counts. Furthermore, such tagged surgical textiles may be part of a tracking system in which specialized scanners may be used to scan the patient and identify when the lagged surgical textiles are retained in the patient. However, as both of these approaches require exclusive use of tagged surgical textiles in order to be effective, these approaches prevent medical staff from using surgical textiles of their choosing. Additionally, the specialized surgical textiles are more expensive than regular surgical textiles and require pairing with scanners and/or other equipment for textile tracking, thereby significantly increasing costs for hospitals and other medical institutions. Thus, it is desirable to have new and improved systems and methods for tracking surgical items.

SUMMARY

Generally, in some variations, a computer-implemented method for tracking surgical textiles includes receiving a first image including a first textile-depicting image region, receiving a second textile-depicting image region, measuring a likelihood that the first and second image regions depict at least a portion of the same textile where the measure of likelihood is at least partially based on a first aspect of the image region and a second aspect of the second image region, and incrementing an index counter of the measure of likelihood does not meet a predetermined threshold. The index counter may be displayed on a display for a user, or otherwise communicated to a user to indicate a textile count.

In another variation, a computer-implemented method for tracking surgical textiles includes receiving a first image including a first textile-depicting image region, receiving a second image including a second textile-depicting image region, defining at least one classification feature at least partially based on a first aspect of the first image region and or a second aspect of the second image region, and measuring a likelihood that the first and second image regions depict at least a portion of the same textile, where the measure of likelihood is based at least in pan on the classification feature, such as by using a machine learning classification algorithm.

In some variations, the one or mote classification features may be based on keypoints, or points of interest, that characterize the textile-depicting image regions in the images. For example, the keypoints may be generated based on a feature extraction technique, which may additionally generate a respective feature descriptor (e.g., a vector) for each keypoint that includes features describing the keypoint. The keypoints for two images under analysis may be correlated or matched based on their feature descriptors, such as with a K-nearest neighbor algorithm or other suitable algorithm. Additionally, one or more various classification features may be generated based on the keypoints. For example, a classification feature may be at least partially based on a numerical difference between the feature descriptors for the matched first and second keypoints. As another example, a classification feature may be at least partially based on a number of predicted matches of first and second keypoints between the two images. As yet another example, a classification feature may be at least partially based on a goodness of fit for a homography transform relating the matched first and second keypoints. Another example of a classification feature is based on a consensus voting for an overall angle of rotation between the matched first and keypoints that is predicted with a voting technique.

Additionally or alternatively, the one or more classification features may be based on aspects characterizing a fluid pattern in the depicted surgical textiles. For example, a classification feature may be at least partially based on area of fluid depicted in the first image region and/or area of fluid depicted in the second image region. In another example, a classification feature may be at least partially based on quantified measures of a fluid component (e.g., hemoglobin mass) depicted in the first image region and/or second image region.

In some variations, the measure of likelihood may be generated based on a classification algorithm applied to the one or more classification features. Two or more images may be classified as potentially depicting at least a portion of the same textile if the measure of likelihood meets the predetermined threshold. The measure of likelihood that the first and second image regions depict at least a portion of the same textile, and/or a classification of the first and second images as potentially depicting duplicate textiles, may be communicated to a user. Furthermore, the method may include prompting the user to confirm whether the first and second image regions depict at least a portion of the same textile. Based on the user's confirmation, the index counter may be decremented and or at least one of the deemed duplicate images may be deleted from a memory, storage device, and/or display.

In another variation, a computer-implemented method for tracking surgical textiles includes receiving a first image comprising a first textile-depicting image region, receiving a second image comprising a second textile-depicting image region, warping at least one of the first and second image regions such that the first and second image regions have corresponding textile-depicting pixels (or pixel groups); and measuring a likelihood that use first and second image regions depict at least a portion of the same textile. The measure of likelihood may be based at least in part on similarity between the corresponding textile-depicting pixels or pixel groups. Furthermore, warping at least one of the first image region and the second image region may include determining a set of one or more textile corners in the first image region or the second image region and mapping the set of textile corners onto a known shape.

Generally, in some variations, a system for tracking surgical textile may include a processor configured to receive a first image comprising a first textile-depicting image region, receive a second image comprising a second textile-depicting image region, define at least one classification feature at least partially based on a first aspect of the first image region and/or a second aspect of the second image region, and measure a likelihood that the first and second image regions depict at least a portion of the same textile, wherein the measure of likelihood is based at least in part on the classification feature. The processor may, in some variations, be further configured to perform the above-described method. Furthermore, the system may include an optical sensor configured to capture images and/or a display configured to display the index counter and/or images.

In another variation, a system for tracking surgical textiles may include a processor configured to: receive a first image comprising a first textile-depicting image region, receive a second image comprising a second textile-depicting image region, and measure a likelihood that the first and second image regions depict at least a portion of the same textile. In this variation, the measure of likelihood is at least partially based on a first aspect of the first image region and a second aspect of the second image region. The processor may be further configured to increment an index counter if the measure of likelihood does not satisfy a predetermined threshold. Furthermore, the system may include an optical sensor configured to capture images and/or a display configured to display the index counter and/or images.

In another variation, a system for tracking surgical textiles may include a processor configured to receive a first image comprising a first textile-depicting image region, receive a second image comprising a second textile-depicting image region, warp at least one of the first and second image regions such that the first and second image regions have corresponding textile-depicting pixels (or pixel groups), and measure a likelihood that the first and second image regions depict at least a portion of the same textile, in this variation, the measure of likelihood is based at least in part on similarity between the corresponding textile-depicting pixels or pixel groups. Furthermore, the processor may be configured to warp at least one of the first image region and the second image region by determining a set of one or more textile corners in the first image region or the second image region and mapping the set of textile corners onto a known shape.

BRIEF DESCRIPTION OF THE DRAWINGS

FIG. 1 is an illustrative schematic of one variation of a system for tracking surgical items.

FIG. 5 is a table of exemplary classification features in one variation of a method for tracking surgical items.

FIG. 10 is a table summarizing results of exemplary implementations of a method for tracking surgical items as described herein.

DETAILED DESCRIPTION

Figure 2:
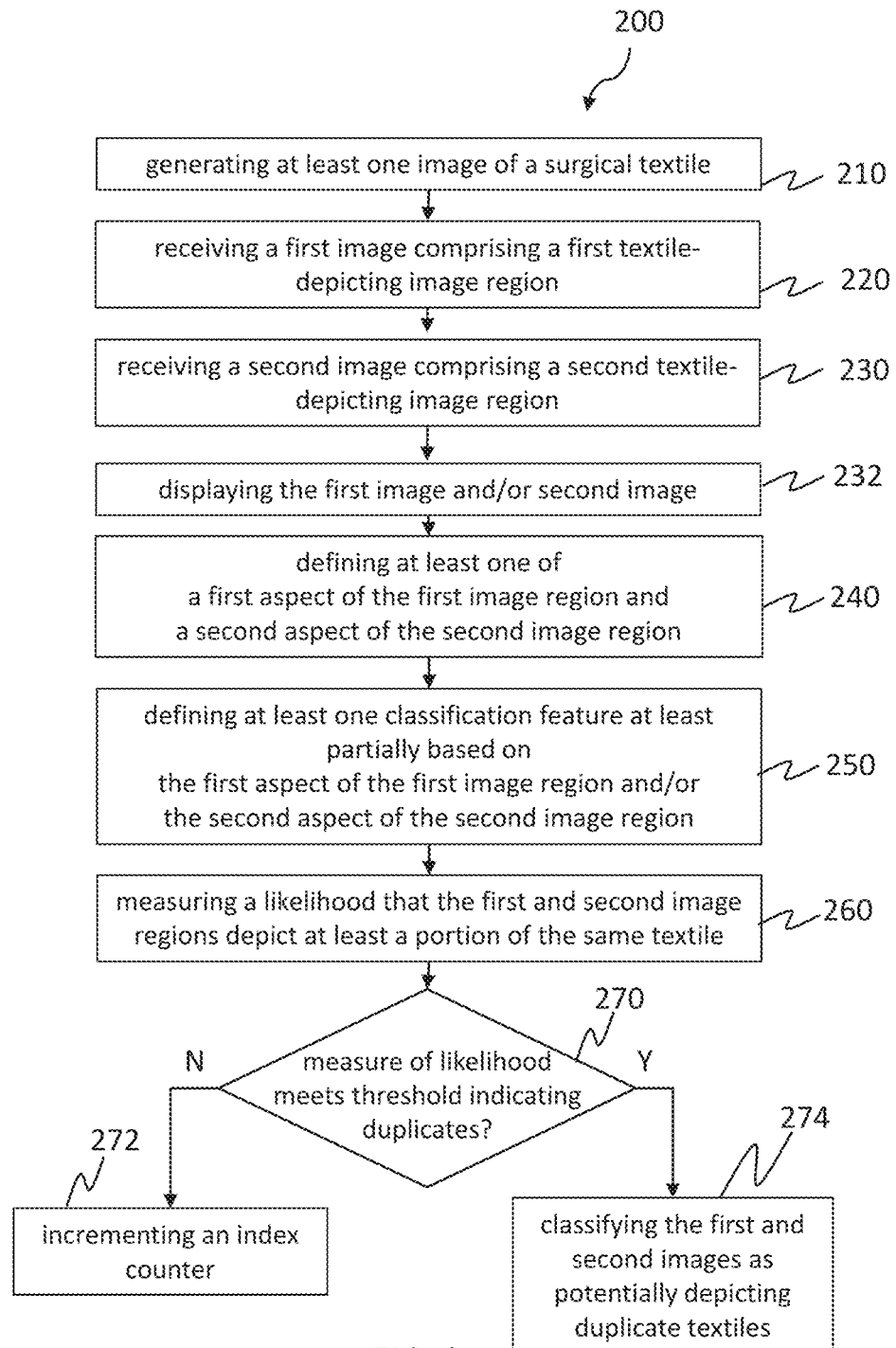
FIG. 2 is a flowchart schematic of one variation of a method for tracking surgical items.

Examples of various aspects and variations of the invention are described herein and illustrated in the accompanying drawings. The following description is not intended to limit the invention to these embodiments, but rather to enable a person skilled in the art to make and use the invention.
Overview Generally, the methods and systems described herein may be used to track (e.g., count) surgical items. For example, the methods and systems may be used to count surgical textiles that have been used at a surgical site, by analyzing optical images depicting the textiles and accounting for potential repeated or duplicate imaging of textiles. Furthermore, the methods and systems may be used in conjunction with other methods and systems used to assess fluids that are lost by a patient during a surgical procedure, based on optical images depicting surgical textiles containing fluids collected by the patient.

The methods and systems may be used in a variety of settings, including in a hospital or clinic setting (e.g., operating or clinical setting), a military selling (e.g., battlefield), or other suitable medical treatment settings. Tracking the surgical items may, for example, enable a more accurate count of the surgical items, which may help avoid inadvertent retention of surgical items in the patient following the surgical procedure. Although. Use methods and systems described herein are primarily described with reference to tracking surgical textiles such as surgical sponges, it should be understood that in other variations, they may additionally or alternatively be used to track other items (e.g., surgical instruments).

The methods described herein may be computer-implemented and performed at least in part by one or more processors. For example, as shown in FIG. 1, in one variation, the method may be performed at least in part by a computer device such as a mobile device 150 (e.g., tablet, smartphone, etc.) that is configured to capture images of one or more surgical textiles in an operating room or other medical site. However, some or all of the method may be performed by one or more processors that are separate from the mobile device 150 (e.g., on-site in the operating room or remotely outside the operating room). Other aspects of variations of methods and systems for tracking surgical items are described in further detail below.

During a medical procedure, extracorporeal fluids (e.g., blood) that are lost by the patient may be collected with surgical textiles, such as surgical sponges, surgical dressings, surgical towels, and/or other textiles. An image (e.g., single image or an image frame from a video feed) may be taken of at least a portion of a surgical textile placed in the Held of view of a camera, and this process may be repeated for multiple surgical textiles. The image may be analyzed to quantify an aspect of the fluid in the depicted surgical textile, such as an amount (e.g., mass, weight, volume) of fluid and/or amount or concentration of a fluid component in the fluid. For example, the image may be an optical color image, and pixel color values may be correlated to an estimated or predicted blood component concentration (e.g., with template matching techniques and/or parametric modeling techniques described in further detail below, etc.). Accordingly, analysis of multiple images of soiled surgical textiles may be aggregated into a running total or overall quantification of estimated amount of fluid loss and or fluid component loss (e.g., blood or hemoglobin) by the patient during the procedure.

Furthermore, since each used or soiled surgical textile may be imaged to facilitate analysis of its fluid or fluid component content, the number of images may generally correlate with the number of used surgical textiles and thus be used as a basis for determining a count of surgical textiles (e.g., for tracking surgical textiles before and after a medical procedure). However, there is a possibility that a surgical textile may be inadvertently imaged multiple times (e.g., if a user forgets that a surgical textile has already been imaged), which may lead to an inaccurate surgical textile count and/or an inaccurate running total or overall quantification of fluid loss and or fluid component loss by the patient (e.g., due to "double-counting" one or more textiles). To counteract these consequences of inadvertent duplicate imaging, one or more of the images may be analyzed to determine a measure of likelihood that the image depicts the same surgical textile as another image. For example, although generally each new image obtained may correspond to an increase in the count of surgical textiles (e.g., that have been extracted from the patient or sterile area for the surgical procedure for an "after" count), the count may be adjusted based at least in part on the measure of likelihood that a surgical textile has been imaged more than once. A detection of a potential duplicate image of a surgical textile may, for example, trigger a prompt to the user to confirm whether the surgical textile has been imaged more than once. As another example, detection of a potential duplicate image of a surgical textile may automatically withhold from incrementing a count and/or automatically withhold (from a running total) an estimated quantity of fluid or fluid component in that surgical textile.

Furthermore, while in some variations the methods described herein may be used to track surgical textiles within the same surgical procedure (or surgical session), in other variations the methods described herein may additionally or alternatively be used to track surgical textiles among different procedures or sessions. Surgical textiles may inadvertently travel between different surgical sessions (e.g., on a nurse or other person moving between different rooms). This may lead to inaccurate textile counts in its origin session and or destination session, such as due to inadvertent duplicate imaging of the traveling textile in its origin and/or destination sessions. Accordingly, in some variations the methods described herein may compare textile-depicting images obtained from different surgical sessions and stored (e.g., on a server or other suitable data storage device) to track surgical textiles within one or more medical environments such as a hospital. For example, a first image associated with a first surgical procedure may be compared with one or more images associated with other surgical procedures performed within a suitable window of lime (e.g., within a preceding or surrounding period of lime of 4 hours, 8 hours, 12 hours, 24 hours, etc.), in order to predict whether a textile has been imaged more than once within the window of time. Such cross-procedural image comparisons using methods described herein may be used to identify images that were taken during different surgical procedures and likely depict at least a portion of the same traveling surgical textile.

Furthermore, traveling textiles may lead to inaccurate textile counts in both its origin and destination sessions, such as due to incorrect determination of a retained textile in the patient due to the textile's inadvertent absence in the origin session's textile count, incorrect accounting for all textiles removed from the patient due to the textile's inadvertent presence in the destination session's textile count, etc. Surgical textiles may, in some variations, be tagged with a unique identifier such as with infrared (IR) and/or ultraviolet (UV)-detectable fluid creating a unique fluid pattern on each textile. The unique fluid patterns may also be associated with a particular surgical procedure. Accordingly, in some variations, the methods described herein may compare (e.g., with pattern recognition techniques) textile-depicting IR and or UV images obtained from different surgical sessions and stored, to track surgical textiles across different surgical sessions within one or more medical environments. Such cross-procedural image comparisons using methods described herein may be used to identify images that were taken during different surgical procedures and likely depict at least a portion of the same traveling surgical textile.

Although variations of the methods are primarily described herein as relating to tracking surgical textiles, it should be understood that in other variations, the method may additionally or alternatively be used to track other items using optical images in a similar manner. For example, the method may lie used to track surgical instruments and/or other surgical items in order to further reduce the risk of foreign objects retained in the pattern.

Methods for Tracking Surgical Textiles

As shown in FIG. 2, in some variations, a method 200 for tracking surgical textiles or other items may include receiving a first image comprising a first textile-depicting image region 220, receiving a second image comprising a second textile-depicting image region 230, measuring a likelihood that the first and second image regions depict at least a portion of the same textile 250; and incrementing an index counter 272 if the measure of likelihood does not meet a predetermined threshold (270). The measure of likelihood may, in some variations, be at least partially based on a first aspect of the first image region and a second aspect of the second image region. For example, the aspects of the textile-depicting image regions may uniquely characterize the fluid pattern in the depicted surgical textile to some manner, similar to a bar code or other unique identifier. As shown in FIG. 2, the method may include comparing the measure of likelihood of duplicate imaging to a predetermined threshold (270), where the threshold is a cutoff for classifying an image pair as "not duplicate" or "potentially duplicate" When it is more likely that the surgical textile has not been previously imaged, the image pair may be classified as "not duplicate" and a surgical textile count may be incremented. In contrast, when it is more likely that the surgical textile has been previously imaged, the image pair may be classified as "potentially duplicate" and the surgical textile count may remain unchanged, at least until a user has confirmed whether duplicate imaging has occurred.

While the method is primarily described herein with reference to a comparison of two images with respective textile-depicting image regions, it should be understood that in practice, more than two images may be compared in a similar manner. For example, after receiving each image, one or more aspects of the image may be stored and associated with that image (e.g., with a hash function or other suitable data mapping, which may enable faster data lookup). To predict whether any two images depict the same textile, one or more classification features for every possible pair of images may be generated (e.g., a newly received image may be compared to every previously-received image, or all possible pairs may be compared after all images are received) and analyzed as described below.

Images

In some variations, as shown in FIG. 2, the method 200 may include generating or obtaining at least one image of a surgical textile 210. Generating images of surgical textiles functions to provide evidential support for a count of surgical textiles. Upon generation, the images may be stored in a database in a suitable date storage medium (e.g., local or remote). Receiving a first image 220 and receiving a second image 230 may include receiving the image from memory or other suitable storage. In some variations, however, not every step depicted in FIG. 2 need be performed in the depicted order. For example, the images may have been previously acquired and stored in a storage medium (thereby omitting generating the images directly). Each image may include the entire surgical textile or only a portion of the surgical textile. The surgical textile may be, for example, a surgical sponge, dressing, towel, or other suitable textile.

Each image (e.g., a single still image or an image frame from a video feed) may include an image region depicting at feast a portion of the surgical textile placed in the held of view of a camera. The camera may be in a handheld device or mobile device (e.g., tablet), a camera mounted on a tripod at approximately torso height or at a suitable height in another suitable manner, an overhead camera, etc. For example, a camera in a handheld device may be mounted such that the camera faces a person that holds the surgical textile in front of his or her body, or holds the surgical textile against a wall.

In some variations, the surgical textiles may be positioned and oriented in at least a partially consistent manner for imaging, which may improve accuracy in detecting whether duplicate imaging of textiles has occurred. For example, the surgical textiles may be imaged while held generally perpendicular to the optical axis of a camera, which may help reduce out-of-plane orientation differences among images. As another example, surgical textiles may be imaged while positioning textile reference markers (e.g., a blue ribbon on one edge of the textile, tag or other marker on one corner of the textile, etc.) in a consistent orientation relative to the camera's field of view, which may help reduce rotational orientation differences among images. As another example, the corners of the textiles may be located in each image and used to warp images such that the textiles are depicted as having approximately the same shape (e.g., square rectangular, etc.), such as with warping methods described in further detail below, such that the images can be compared in various ways described herein.

The images may be optical images capturing color characteristics, with component values in a color space (e.g., RGB, CMYK, etc.) for each pixel. The image may be stored in memory or a suitable data storage module (e.g., local or remote) and processed. Processing the image may include normalizing the color characteristics of the image based on a set of one or more optical fiducials (e.g., a color fiducial). The color fiducial may represent, for example, one or more red hoes (e.g., a grid including boxes of different red hues). Normalization of the image may utilize the color fiducial to compensate for variations in lighting conditions throughout an operation, to artificially match lighting conditions in the image to a template image, to artificially match lighting conditions in the image to a light condition-dependent fluid component concentration model, etc. For example, normalizing the image may include identifying a color fiducial captured in the image, determining an assigned color value associated with the identified color fiducial, and adjusting the image such that the color value of the color fiducial in the image substantially matches the assigned color value associated with the color fiducial. The assigned color value can, for example, be determined by looking up the color fiducial in a database (e.g., identified by code, position within a set of color fiducials, position relative to a known feature of the conduit, etc.). Adjustments to the image can include, for example, adjustment of exposure, contrast, saturation, temperature, tint, etc.

In some variations, the method may include identifying a textile-depicting image region in one or more of the images. For example, identifying a textile-depicting image region may include applying an edge detection technique, applying template matching techniques, and/or applying any suitable machine vision techniques to identify boundaries of the textile-depicting image region. In another variation, identifying a textile-depicting image region may include defining the textile-depicting image region's boundaries at least partially based on user input. For example, the user input may designate a portion of a displayed image as the textile-depicting image region (e.g., the user may define boundaries of the image region on a touchscreen display such as by touching the screen and dragging a window or frame to a size and location of a desired textile-depicting image region, or touching the screen to place markers outlining the boundaries of a desired textile-depicting image region).

Figure 8:
FIG. 8 is an exemplary display of images depicting surgical textiles.

Furthermore, as shown in FIG. 2, the method may include displaying at least one of the first image and the second image 232 (or alternatively, an isolated textile-depicting image region of the images). The images may be displayed, for example, on a display on a mobile device (e.g., tablet) or any other suitable display. As shown in FIG. 8, the various images generated may be displayed in a suitable array (e.g., chronological order) for a user to view.

Aspects of Image Regions and Classification Features

As shown in FIG. 2, the method may include defining at least one of a first aspect of the first textile-depicting image region and a second aspect of the textile-depicting second image region 240. The first and second aspects are characterizations of at least a portion of the first and second images, respectively, and serve as a basis for generating a measure of likelihood that the first and second images depict the same surgical textile. In other words, the appearance (e.g., fluid pattern) of the surgical textile may serve as a unique identifier for the surgical textile, such that similar-looking surgical textiles depicted in different images may indicate duplicate imaging of the same textile.

Furthermore, the method may include defining at least one classification feature 150 at least partially based on the first aspect of the first image region and/or the second aspect of the second image region. Examples of classification features are provided in FIG. 5. The kind of classification feature may depend at least in pan on the kind of aspects of the textile-depicting image regions that have been defined, as described in further detail below.

Keypoints

An image of a surgical textile or object has keypoints, or points of interest, which can be extracted and used to collectively describe or characterize the imaged object. Furthermore, each keypoint may have a corresponding feature descriptor (e.g., a vector including a set of values), that describes the keypoint. Generally, in some variations of the method, a prediction of whether two or more images depict the same textile may be at least partially based on a comparison between keypoints identified in the images.

Figure 3:
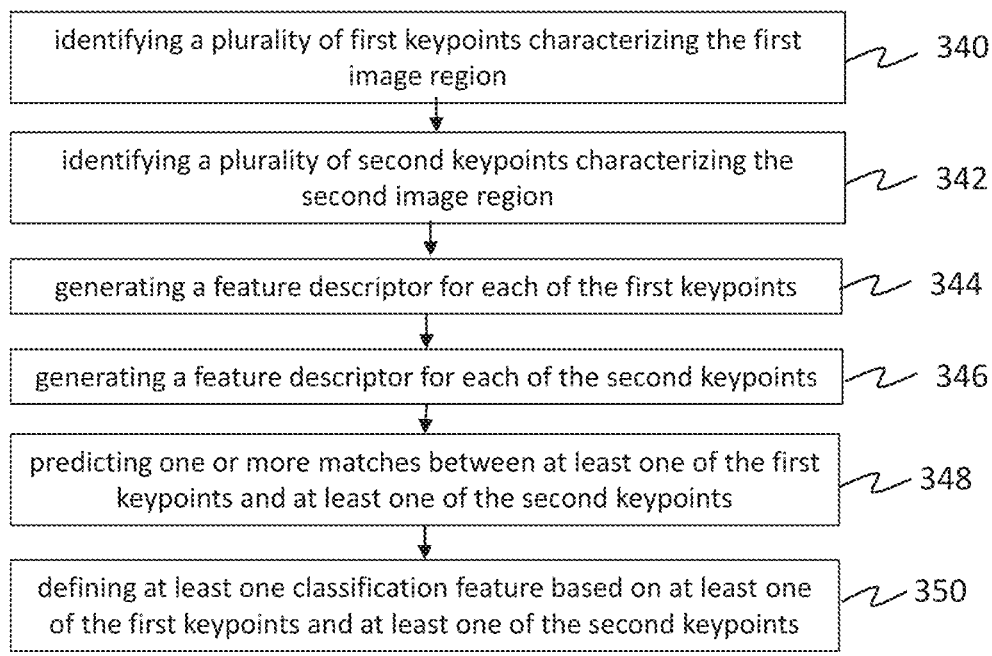
FIG. 3 is a flowchart schematic of an exemplary variation of a method for tracking surgical items including defining at least one classification feature based on extracted features and keypoints in mage regions.

Accordingly, in some variations, as shown in FIG. 3, the method may include identifying a plurality of first keypoints characterizing the first image region 340 in the first image, identifying a plurality of second keypoints characterizing the second image region 342 in the second image, generating a feature descriptor for each of the first keypoints 344, and generating a feature descriptor for each of the second keypoints 346. One or more classification features for predicting duplicate imaging may then be based on at least some of the first and/or second keypoints (350).

The method may include applying a feature extraction technique such as a scale-invariant feature transform (SIFT), a speeded up robust features (SURF) technique, or any other suitable feature extraction technique in order to identify keypoints and or generate feature descriptors for the keypoints. Other examples of feature extraction techniques include but are not limited to: histogram of oriented gradients (HOG), features from accelerated segment test (FAST), local energy-based shape histogram (LESH), gradient location-orientation histogram (GLOH), fast retina keypoint (FREAK), Oriented FAST and Rotated BRIEF (ORB), Texton Maps, and learned keypoint-detectors and descriptor-generators based on trained (or unnamed) neural networks, using supervised, unsupervised, or semi-supervised learning. Furthermore. SIFT descriptors and/or keypoints, or any of the above descriptors and or keypoints, may be extracted from the depth map, possibly after a defending step that fits a linear or non-linear surface to the depth map of the sponge and subtracts it from the depth map so that the only remaining depth variation is substantially due to local 3D textures in the sponge. These 3D-texture descriptors may be extracted in addition to or in combination with any color-based descriptors. Additionally, video-based descriptors may be extracted by applying any of the above descriptor methods to the optical flow vector field computed over any number of frames. Alternatively, or in addition to optical-flow-based methods, the keypoints may be tracked across multiple frames and their descriptors in the frames may be concatenated, or the change in a descriptor across frames may be recorded. Any other video-based features, keypoints, or descriptors may additionally or alternatively be used. In some variations (e.g., at least in instances in which textiles are fully or nearly fully saturated with fluid), small spatial changes in color (which may not visible to the human eye but may be captured in the optical image) may be magnified by image processing before applying the feature extraction technique.

For example, in one variation, feature descriptors for characterizing keypoints or points of interest in an image region may be generated with a SIFT-based process. SIFT feature descriptors for characterizing points of interest in an image may be invariant to scale and rotation, and may be partially invariant to illumination changes as well. The SIFT-based process may, for example, identify a set of keypoints or points of interest in the first image region, then assign a set (or vector) of feature descriptors for the identified keypoints. Generally, the method may perform scale-space extreme detection, such as by convolving the first image with Gaussian filters at different successive scaling parameters, taking the difference of the successive Gaussian-blurred (Difference of Gaussian) images that are derived from the first image, and identifying local extrema (minima and/or maxima) of the Difference of Gaussian images across scale and space to identify candidate keypoints. The method may then perform keypoint localization (interpolating data near each candidate keypoint to accurately determine its position in the image) and refine the list of candidate keypoints (e.g., by discarding keypoints such as those having low contrast or those present on an image edge). The method may assign an orientation to each of the remaining keypoints based on directions of local image gradients. The identified keypoints may, as a result of these steps, may be substantially invariant to location in the image, as well as scale and rotation of the image. Finally, a feature descriptor may be generated for each identified keypoint such that the feature descriptors provide for invariance to other variations such as illumination, 3D rotation of the image, etc. for example, for each keypoint, the method may begin generating a feature descriptor by taking a 16 pixel×16 pixel neighborhood around the keypoint, dividing the neighborhood into 16 sub-blocks of 4 pixel×4 pixel size, and creating an 8-bin orientation histogram for each sub-block, thereby creating a total of 128 bin values. The feature descriptor for the keypoint may include the 128 bin values. Alternatively, other sizes of neighborhood and or sub-blocks may be used to generate the feature descriptor. The above-described SIFT-based process may be performed to identify keypoints and/or generate feature descriptors in all images obtained or received. Furthermore, in some variations, in addition to generating and retaining the feature descriptors, the orientations and/or scales of the keypoints (and/or other pertinent information) may be retained, which may, for example, enable determination of additional image-matching features.

Additionally or alternatively, other suitable feature extraction techniques may be used to identify keypoints and/or generate feature descriptors and or other suitable information.

As shown in FIG. 3, following generation of a feature descriptor for each of the first keypoints (344) and generation of a feature descriptor for each of the second keypoints (346), the method may include predicting one or more matches between at least one of the first keypoints and at least one of the second keypoints 350. Generally, this prediction functions to identify pairwise correspondence between points of interest in the first and second textile-depicting image regions, based on similarity of their keypoints' feature descriptors. For example, the feature descriptors for the first keypoints and the feature descriptors for the second keypoints may be compared in an attempt to find the closest overall numerically-similar features across all the keypoints between the two textile-depicting image regions (e.g., with a K-nearest neighbor technique). As depicted schematically in FIG. 4, some or all of the first keypoints in the first image region 412 in the first image 410 may be matched to corresponding second keypoints of the second image region 422 in the second image 420. For example, keypoints 414a, 414b, and 414c in the first surgical-depicting image region 412 may be matched to keypoints 424a, 424b, and 424c in the second surgical-depicting image region 422, respectively.

Furthermore, the method may include defining at least one classification feature at least partially based on the first and second keypoints 350. Examples of classification features based on the first and second keypoints are shown in FIG. 5. In one variation, the method may include defining a classification feature (labeled as distanceFearures in FIG. 5) at least partially based on a difference between the feature descriptors for matched first and second keypoints 361. In other words, the classification feature may characterize the distance between the feature descriptors in the descriptor space for the pluralities of first and second keypoints. For example, an overall distance or difference between the feature descriptor values for a first keypoint and the feature descriptor values for a second keypoint (where the first and second keypoints have been matched) may be determined based on root mean square deviation (RMSD) or root mean square error (RMSE), or other suitable measure of distance. RMSD or RMSE may be determined for every matched pair of first and second keypoints for the first and second images, then aggregated (e.g., averaged) to provide a measure of overall difference between the plurality of first keypoints and the plurality of second keypoints. Generally, the smaller the difference between feature descriptors, the more likely the first and second image regions depict the same surgical textile. Furthermore, in some variations, robust aggregation methods (e.g., leaving out the 10% largest and smallest distances, or computing the median rather than average distance, etc.) may be used to make this classification feature less prone to spurious matches.

Figure 4:
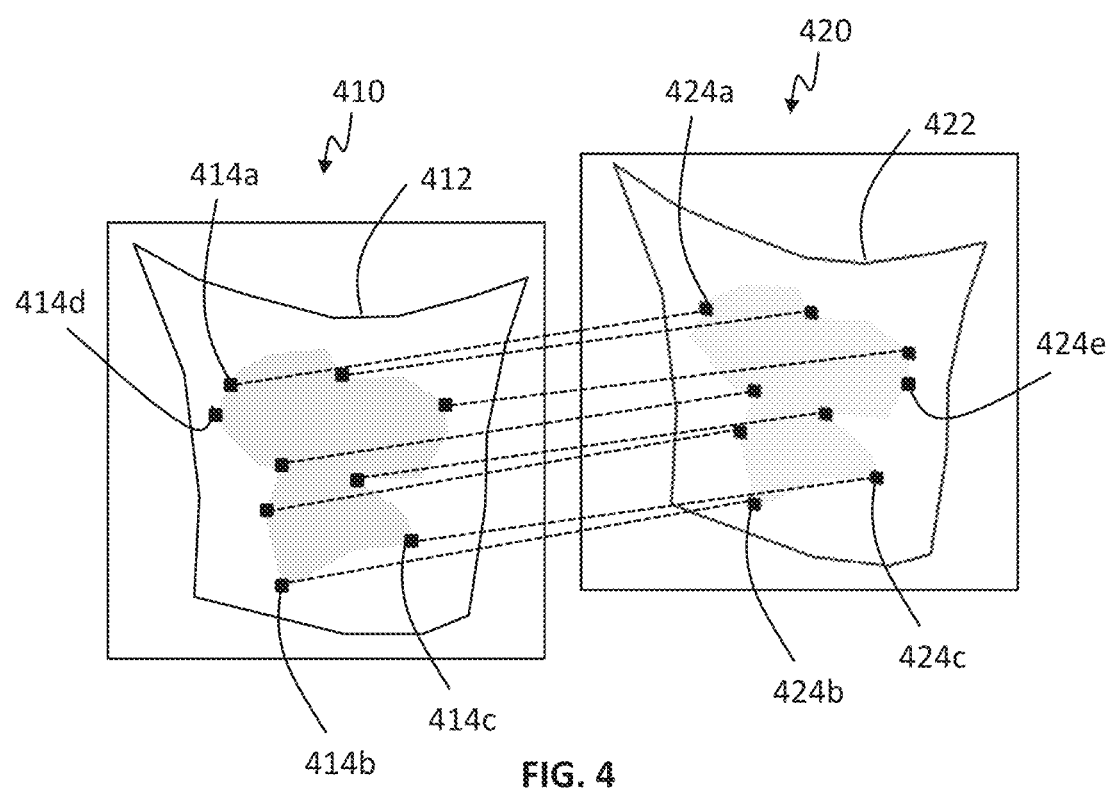
FIG. 4 is an illustrative schematic of two images with matching and non-matching keypoints.

In another variation, the method may include defining a classification feature (labeled as goodnessHomography in FIG. 5) at least partially based on a goodness of fit of a tomography transform relating the matched first and second keypoints 362. Generally, a tomography transform may be configured to model how each of the plurality of first keypoints in the first image region may be mapped to its matching second keypoint in the second image region, or vice-versa. For example, as shown in FIG. 4, first keypoints (e.g., 414a, 414b, and 414c) in the first image region 412 may correspond to matching second keypoints (e.g., 424a, 424b, and 424c, respectively) in the second image region 422, where the second image region 422 may be distorted relative to the first image region 412 (e.g., rotated or angled away from the camera differently). Given the location coordinates $(x_j, y_j)$ of the first keypoints in the first image region 412 and the location coordinates $(x_j, y_j)$ of the second keypoints in the second image region 422, a homography transform (e.g., a matrix) may mathematically describe the translation, rotation, scale, out-of-plane orientation changes, and other causes of distortion between the sets of $(x_j, y_j)$ and $(x_j, y_j)$. However, the homography transform may be an imperfect fit across all of the matched pairs of first and second keypoints. Accordingly, in some variations, the method may include fitting a homography transform relating the matched first and second keypoints, and defining a classification feature at least partially based on the goodness of fit of the homography transform over all matched pairs of first and second keypoints. Any suitable goodness of fit tests may be used to generate a measure of the goodness of fit of the homography transform, such as $R^2$, robust-$R^2$, Spearman's rho, or based on percentage of keypoints within some predefined distance (e.g., in (x, y) space or other coordinate system) of their match, or any other suitable test. Furthermore, in another variation, distance in feature descriptor space may be combined with distance in (x, y) space (or other coordinate system) to create an informative goodness-of-fit measure (e.g., computing $R^2$ but weighting each keypoint's contribution by exp(−descriptor_distance) (or other suitable weighting factor) so that keypoints with less similar descriptors have less contribution to the goodness of fit. In yet another variation, if a robust fitting method such as RANSAC or Hough transform is used to fit the homography, then one of the outputs of the fitting will be a set of inlier points, and the size of this set relative to the size of the inputs may be used as a goodness-of-fit metric. Generally, the better the goodness of fit of the homography transform, the more likely the first and second image regions depict the same surgical textile.

In some variations, the method may include incorporating one or more mathematical models or functions to compensate for potential textile shape variations between images. For example, the same surgical textile may not only undergo translation, rotation, scale, and/or out-of-plane orientation changes, etc., but additionally or alternatively may undergo internal displacements (e.g., stretching or sagging, depending on how taut the textile is held during imaging). To compensate for potential shape variations, the method may, in some variations, include modifying and/or supplementing the homography transform to account for stretch, slack, etc. For example, the homography transform may be modified to incorporate a function configured to model curvature of a textile, such as curvature based on displacement of an edge of the textile (e.g., vertical displacement of an upper drooping edge of the textile), distance between reference markers placed on the textile, etc. As another example, the homography transform may be supplemented with a function configured to model curvature of a textile, where the function is applied separately (e.g., after) the homography transform to relate or map the matched pairs of first and second keypoints to each other.

In another variation, the method may include defining a classification feature (labeled as angleHough in FIG. 5) at least partially based on a measure of confidence for a predicted overall angle of textile rotation 363 between the first and second images, where me predicted angle of rotation may be derived from the matched first and second keypoints. The predicted overall angle of rotation may be based on, for example, a Hough transform or other curve-fitting or line-fitting technique. The Hough transform is a voting technique that, when applied to the matched first and second keypoints, may probabilistically predict an angle of rotation of the depicted textile based on the matched keypoints. In some variations, the consensus voting ratio (generally indicating the proportion of keypoints that "vote" for the most likely angle of rotation) may be used as a measure of confidence that the predicted overall angle of rotation is correct. Generally, the higher the consensus voting ratio, the more likely the first and second image regions depict the same surgical textile.

In another variation, the method may include defining a classification feature (labeled as measureMatches in FIG. 5) at least partially based on a measure of predicted matches of first and second keypoints 364 between the first and second images. Not all keypoints in the first textile-depicting image region will necessarily be matched with a keypoint in the second textile-depicting image region, and vice-versa. For example, as illustrated in FIG. 4, first keypoint 414d in the first image region 412 is not matched with a corresponding second keypoint in the second image region 422. Additionally, second keypoint 424e is not matched with a corresponding first keypoint in the first image region 412. Generally, the greater the measure of predicted matches of first and second keypoints in the first and second image regions, the more likely the first and second image regions depict the same surgical textile. The measure of predicted matches of first and second keypoints may be at least partially based on, for example, a total number of predicted matches, a percentage of first keypoints in the first image that have matches (matched to a keypoint in the second image), a percentage of second keypoints in the second image that have matches (matched to a keypoint in the first image), a ratio between the number or percentage of first keypoints in the first image that have matches and the number or percentage of second keypoints in the second image that have matches, and/or any combination thereof.

In another variation, the method may include defining a classification feature at least partially based on the consistency in the scale of feature descriptors for the matched first and second keypoints. As described above, keypoints in the images may be determined by identifying local extrema in difference of Gaussian images across different scales (different scaling parameters), such that different keypoints may have corresponding feature descriptors with values from different scales. Generally, the more consistent or equal the scale of feature descriptors for the matched keypoints among the first and second images, the more likely the first and second image regions depict the same surgical textile.

In another variation, the method may include defining a classification feature at least partially based on the consistency in an orientation offset of the matched first and second keypoints. As described above, orientations of the keypoints in the images may be retained. Generally, the more consistent or equal the offset in orientation among the matched keypoints between the first and second images, the more likely the first and second image regions in the images depict the same surgical textile.

Global Aspects

In some variations, the first aspect of the first image region and/or the second aspect of the second image region may characterize one or more global aspects of the depicted surgical textile. Global aspects may, for example, characterize (on a larger scale than keypoints described above) the size, shape, or fluid content of a fluid pattern on the depicted surgical textile. Generally, in some variations of the method, a prediction of whether two or more images depict the same textile may be at least partially based on a comparison between the global aspects identified in the images.

Figure 6A:
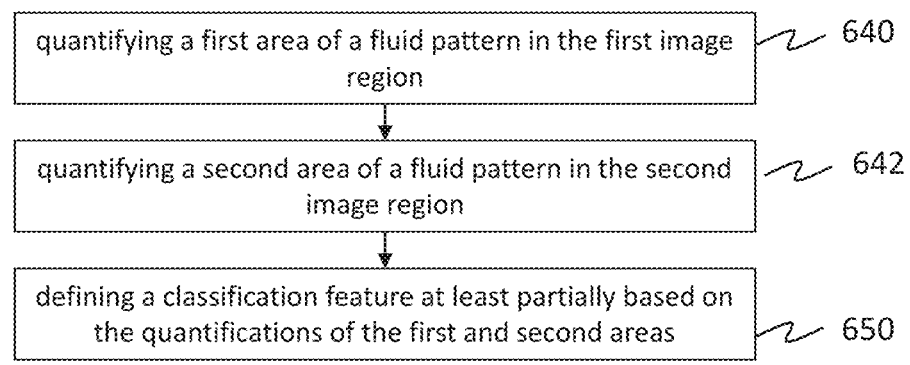
FIG. 6A is a flowchart schematic of an exemplary variation of a method for tracking surgical items including defining at least one classification feature based on area of fluid patterns in the depicted surgical items.

In one variation, the global aspects may characterize an area of a fluid pattern on the depicted surgical textile. For example, as shown in FIG. 6A, the method may include quantifying a first area of a fluid pattern in the first image region 640, quantifying a second area of a fluid pattern in the second image region 642, and defining a classification feature at least partially based on the quantifications of the first and second areas 650. Generally, the classification feature (labeled as fluidRegionRatio in FIG. 5) may indicate level of similarity of the quantifications of first and second areas (e.g., spread of the fluid pattern between the two imaged textiles), where the more similar the quantified first and second areas are, the more likely the first and second image regions depict the same surgical textile.

Figure 6B:
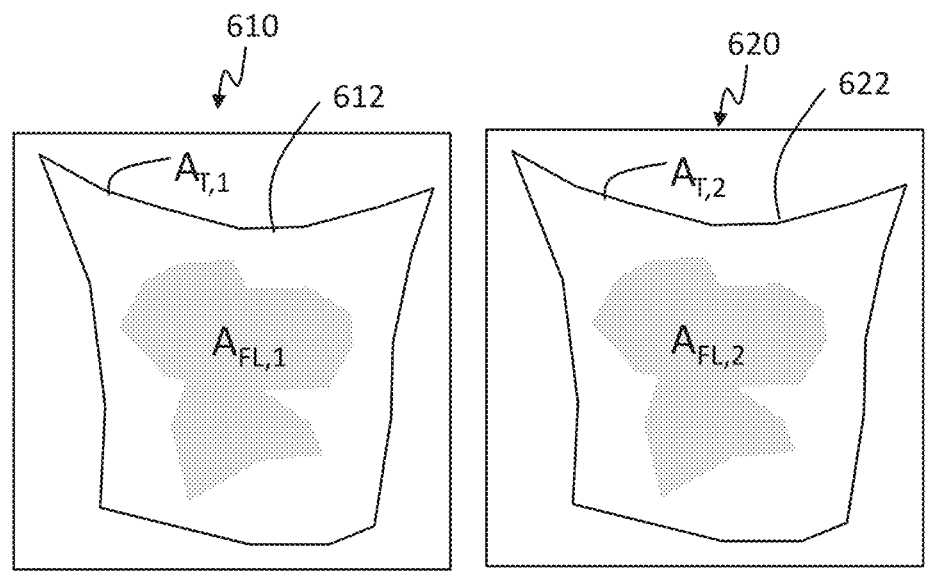
FIG. 6B is a graphical representation of parameters used to define the classification feature shown in FIG. 6A.

As one illustrative example, areas of fluid patterns may be quantified as a ratio between an area of the depicted textile containing fluid and the total area of the depicted textile (e.g., a percentage of textile that is soiled with fluid). Characterizing areas of fluid patterns with such ratios may account for the possibility of surgical textiles being imaged at different camera distances. Generally, for each of the first and second images, the method may include determining an area of the fluid pattern, determining an area of the surgical textile, and determining the ratio of the area of the fluid pattern to the total textile area. The area of the fluid pattern may be based on, for example, the number of pixels in the image region having a color component value (e.g., red) above a predetermined threshold (e.g., "fluid" pixels). The area of the surgical textile may be based on, for example, the number of pixels in the image region previously determined (e.g., by user selection or edge detection techniques) to depict the surgical textile (e.g., "textile" pixels). The quantified area of fluid patterns in a textile-depicting image region may then be based on a ratio of "fluid" pixels to "textile" pixels (or alternatively, vice-versa). Accordingly, with reference to FIG. 6B, quantifying a first area of a fluid pattern in the first image region 640 may include determining a first fluid ratio $R_1$ of the fluid pattern area $A_{FL,1}$ to the total textile area $A_{T,1}$ in the first textile-depicting image region 612. Similarly, quantifying a second area of a fluid pattern in the second image region 642 may include determining a second fluid ratio $R_2$ of the fluid pattern area $A_{FL,2}$ to the total textile area $A_{T,2}$ in the second textile-depicting image region 622. Furthermore, subsequent to determining these ratios for the first image region and for the second image region, the method may include defining a classification feature (labeled as fluid RegionRatio in FIG. 5) at least partially based on a comparison of the ratios (e.g., comparison of the percentage of textile that is soiled with fluid). For example, the classification feature may be based on an absolute difference between the first fluid ratio $R_1$ and the second fluid ratio $R_2$ (e.g., $R_1$ or $R_2$ or vice versa) and or a measure of the difference between the first fluid ratio $R_1$ and the second fluid ratio $R_2$ (e.g., $R_2/R_1$ or $R_1/R_2$).

Alternatively, in another variation, area of a fluid pattern on the depicted surgical textile may be quantified as the fluid pattern area (e.g., absolute number of pixels comprising the fluid pattern in the depicted textile) $A_{FL,1}$ or $A_{FL,2}$. A classification feature may be teed on the difference between the absolute number of "fluid" pixels to the first image region and the absolute number of "fluid" pixels in the second image region, for example, when size of the depicted surgical textile is standardized across all images (e.g., precautions are taken to ensure each textile is imaged from the same camera distance, images or textile-depicting image regions are adjusted to be the same size, etc.).

Figure 7:
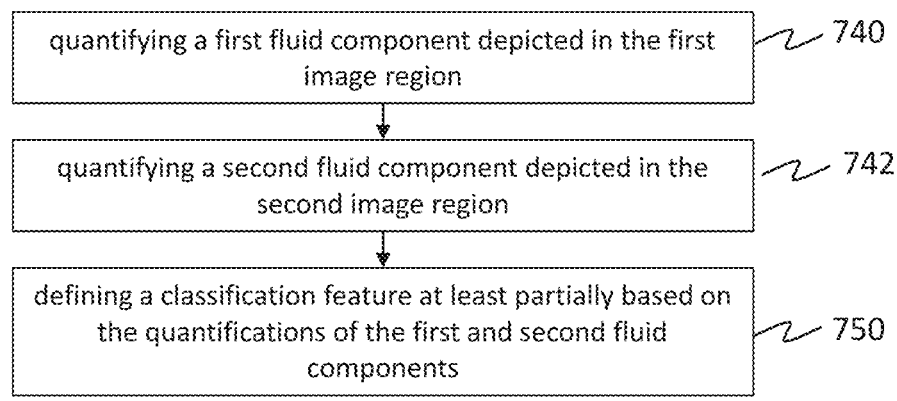
FIG. 7 is a flowchart schematic of an exemplary variation of a method for tracking surgical items including defining at least one classification feature based on quantifications of fluid components in the depicted surgical items.

In another variation, the global aspects may characterize content of a fluid pattern on the depicted surgical textile. For example, as shown in FIG. 7, the method may include quantifying a first fluid component depicted in the first image region 740, quantifying a second fluid component depicted in the second image region 742, and defining a classification feature at least partially based on the quantifications of the first and second fluid components 750. The quantification may measure, for example, mass, weight, volume, concentration, etc. of the fluid component. In some variations in which the fluid in the surgical textile is blood, the fluid component to be quantified may be for example, hemoglobin, red blood cells, or other suitable blood component. For example, the global aspects of the depicted surgical textiles may include estimated hemoglobin mass. Generally, the classification feature may indicate a level of similarity of the content of the fluid pattern depicted in the first and second images, where the more similar the contents are, the more likely the first and second image regions depict the same surgical textile.

For example, to convert pixel color values of the fluid pattern to a fluid component quantity, template matching techniques may include comparing a redness intensity of the image region against redness intensity from template images (e.g., a training set, samples analyzed previously). Each template image may be contained within a library of template images, and may be associated with a known blood, hemoglobin, red blood cell mass or volume, and/or other fluid characteristics. Generally, where the redness intensity of the image region is substantially similar to (and is paired with) a closest-matching template image, the image region may be estimated as depicting the same fluid component quantity as the closest-matching template image.

In one example, K-nearest neighbor methods may be used for the template matching. More specifically, a K-nearest neighbor method may be used to compare the redness intensity of the image region with redness intensity values in the template images. Additionally or alternatively, a K-nearest neighbor method may be used to compare greenness intensity and/or a blueness intensity (e.g., in conjunction with a redness intensity) of pixels in the image region with greenness and/or blueness intensity values of the template images. Thus, the image region may be paired with the closest-matching template image identified with the K-nearest neighbor method, and the image region may be estimated as depicting the same fluid component quantity associated with the closest-matching template image.

In another example, absolute differences in pixel intensities (e.g., in red, green, and/or blue intensities or color values) may be used for the template matching. Such an absolute difference in pixel intensities may be calculated at a wavelength of light that correlates with the fluid component (e.g., at about 400 nm for estimating hemoglobin concentration). More specifically, a sum of absolute differences in pixel intensities may be used to compare pixel intensities between the image region and each template image. The closest-matching template image is identified when the sum of absolute differences is substantially minimal compared to other sums of absolute differences calculated for the image region and other template images. Thus, the image region may be paired with the closest-matching template image identified with the sum of absolute differences method, and the image region may be estimated as depicting the same fluid component quantity associated with the closest-matching template image.

Furthermore, parametric models may be used to convert pixel color values in the image region to a fluid component quantity. Generally, color values of the template images may be used to train or generate a parametric model (mathematical function, curve, or algorithm, etc.) that correlates a pixel color value to a fluid component quantity. The parametric model may take an input of pixel intensities or color values and convert it into an output of an estimated fluid component quantity value.

Additionally or alternatively, in quantifying a fluid component in the first image region and/or second image region, the method may employ any one or more techniques such as those described in U.S. Pat. No. 8,792,693 and/or 8,983,167, each of which is hereby incorporated in its entirety by this reference.

As shown in FIG. 7, subsequent to quantifying a first fluid component depicted in the first image region 740 and quantifying a second fluid component depicted in the second image region 742, the method may include defining a classification feature at least partially based on the quantifications of the first and second fluid components 750. In some variations, the classification feature (labeled as fluidEstimate in FIG. 5) may be at least partially based on a comparison between the quantifications of the first and second fluid components, such as an absolute difference or percentage difference, to indicate similarity in the quantity of the fluid component between the two images.

In another variation, the global aspects may characterize global shapes of a fluid pattern on the depicted surgical textile. For example, global geometric aspects of the fluid pattern on the textiles may be classified and used to characterize each textile-depicting region. For example, generally larger-scale geometric patterns (e.g., "large" patch versus "small" patch in the fluid pattern) may be recognized and stored as a fingerprint or other unique identifier corresponding to each image or image region. Centers and radii of fluid subregions (e.g., blobs) may also be incorporated in characterize the global geometric aspects of the fluid pattern. As another example, the 2D shape of the fluid pattern (or subregions of the fluid pattern) may be identified and transformed with a Fourier transform to create a unique identifier for the fluid pattern or subregion of the fluid pattern, and therefore a unique identifier for each textile-depicting region.

In yet another variation, image aspects may include aspects of a threading pattern on the depicted surgical textile. For example, it may be appropriate in some instances to consider that each surgical textile has a unique thread pattern (e.g., at least on a very fine scale that may be captured in an optical image). Determining or extracting features of the threading pattern may be similar, for example, to feature extraction techniques described above.

Measure of Likelihood of Duplicate Imaging

As shown in FIG. 2, the method may include measuring a likelihood that the first and second image regions depict at least a portion of the same textile 260. Generally, this measure of likelihood of duplicate imaging may be based on the one or more classification features for the first and second images, and may represent a risk that the first and second images depict at least a portion of the same textile, or equivalemly a level of certainty or confidence that the first and second images are not duplicate images.

In some variations, the measure of likelihood of duplicate imaging may be generated with a suitable classification algorithm applied to one or more classification features. For example, for each pair of images under analysis (e.g., the first and second images), such algorithms may take one or more of the classification features described above as inputs, and generate a value indicating the probability that the pair of images depict at least a portion of the same textile. For example, the classification algorithm may include a K-nearest neighbors approach, a decision tree approach, a support vector machine, random forest or extra tree approach, neural network approach (e.g., convolutional neural network approach), etc. The classification algorithm may be a machine learning algorithm that has been trained on previously-generated training data. For example, the classification algorithm may have been trained using a training dataset that includes classification features based on labeled pairs of images, where the labeled pairs of images are either labeled as known "duplicates" (that is, depicting the same textile) or known "not duplicates" (that is, not depicting the same textile). In some variations, the classification algorithm may be trained such that a greater measure of likelihood that a pair of images are duplicates is indicated by a higher numerical score (i.e., the classification algorithm may be trained to classify images as "duplicates"). Alternatively, the classification algorithm may be trained such that a greater measure of likelihood that a pair of images are duplicates is indicated by a lower numerical score (i.e., the classification algorithm may be trained to classify images as "not duplicates"). The measure of likelihood may, for example, range between about 0 and about 1 (or between about 0 and about 100, or any other suitable range). Furthermore, a score output of any suitable classification algorithm may be converted to a probability via methods such as Platt scaling or isotonic regression, etc.

Accordingly, measuring a likelihood that the first and second image regions depict at least a portion of the same textile 260 may include applying a classification algorithm to the at least one classification feature corresponding to the first and second images. The classification algorithm may generate a measure of likelihood that the pair of images depict at least a portion of the same textile, in practice, the classification algorithm may be further applied to classification features for each pair of images received, such that each pair of images has a corresponding measure of likelihood indicating the probability that the pair depicts at least a portion of the same surgical textile. Each measure of duplicate likelihood may then be evaluated such as by comparison to one or more thresholds, as further described below. Additionally, in some variations, the measure of likelihood may be communicated to the user (e.g., visually on a display and/or audibly through a speaker device, etc.) after it is generated.

In some variations, the method may include adjusting the measure of duplicate likelihood based on one or more other risk-based parameters. For example, the measure of duplicate likelihood may be increased or decreased to reflect type of surgical textiles (e.g., it may be harder to distinguish between different instances of one type of textile than between different instances of another type of textile) and/or other risk-based parameters that may not be not accounted for in the classification features and classification algorithms. As another example, multiple classification algorithms may additionally or alternatively be applied to the one or more classification features for each pair of images, resulting in multiple measures of duplicate likelihood that may be averaged or otherwise combined (e.g., to increase confidence level) to generate an aggregate risk score as an adjusted measure of likelihood for each pair of images. In some variations, the adjusted measure of duplicate likelihood may be considered an individual risk score for the pair of images under analysis reflecting the risk that the images depict at least a portion of the same surgical textile.

Evaluation of Measure of Likelihood

As shown in FIG. 2, the method may include comparing the measure of likelihood of duplicate imaging to a predetermined threshold (270), where the threshold is a cutoff for classifying an image pair as "not duplicate" or "potentially duplicate." For example, if the measure of duplicate likelihood (which may be adjusted or not adjusted) does not meet the threshold, then the method may include incrementing an index counter 272, where the index counter tracks surgical textile count. Conversely, if the measure of duplicate likelihood does meet the threshold then the method may include classifying the first and second images as potentially depicting duplicate textiles 274, withholding an increment of the index counter, and/or triggering additional evaluation such as that described below in some variations, the index counter may still increment if the measure of duplicate likelihood does meet the threshold, but may trigger additional evaluation such as that described below.

In some variations, the measure of duplicate likelihood for a pair of images may be compared to one threshold to classify the images into one of two categories: "not duplicates" or "potential duplicates." For example, in variations in which the measure of duplicate likelihood ranges from 0-100 and higher values correspond to higher likelihood of duplicate imaging, an image pair's measure of duplicate likelihood that is less than a threshold of 50 may result in classifying the image pair as "not duplicates," while an image pair's measure of duplicate likelihood that is 50 or more may result in classifying the image pair as "potential duplicates" However, any suitable single threshold on a 0-100 scale may be used (e.g., between about 10 and about 90, between about 25 and about 75, between about 35 and about 65, between about 45 and about 55, etc.), or any suitable threshold in any suitable range (e.g., at about a midpoint of the possible range of values of the measure of duplicate imaging). The threshold may be adjusted for desirable sensitivity. For example, it may be preferable to have more false positives (i.e., incorrect predictions of duplicates) than false negatives to trigger user confirmation of whether duplicate imaging has occurred. Such threshold adjustment may occur based on manual selection by a user, and/or based on certain environmental conditions (e.g., when multiple surgical textiles consistently appear to be fully or nearly fully saturated with fluid, and thus more difficult to distinguish from each other).

Alternatively, in some variation, the measure of duplicate likelihood for a pair of images may be compared to multiple thresholds to classify the images into more than two categories. For example, two thresholds may classify an image pair's measure of duplicate likelihood as representing a "low", "medium", or "high" risk for being potential duplicates (e.g., on a scale of 0-100, a measure of duplicate likelihood below a first threshold of about 25 may correspond to a low risk for duplicate imaging, a measure of duplicate likelihood above a second threshold of about 75 may correspond to a high risk for duplicate imaging, and a measure of duplicate likelihood between the first threshold 25 and the second threshold 75 may correspond to a medium risk for duplicate imaging). Other suitable numbers and types of thresholds may be used to classify the image pairs into any suitable number or type of risk categories.

Figure 9A:
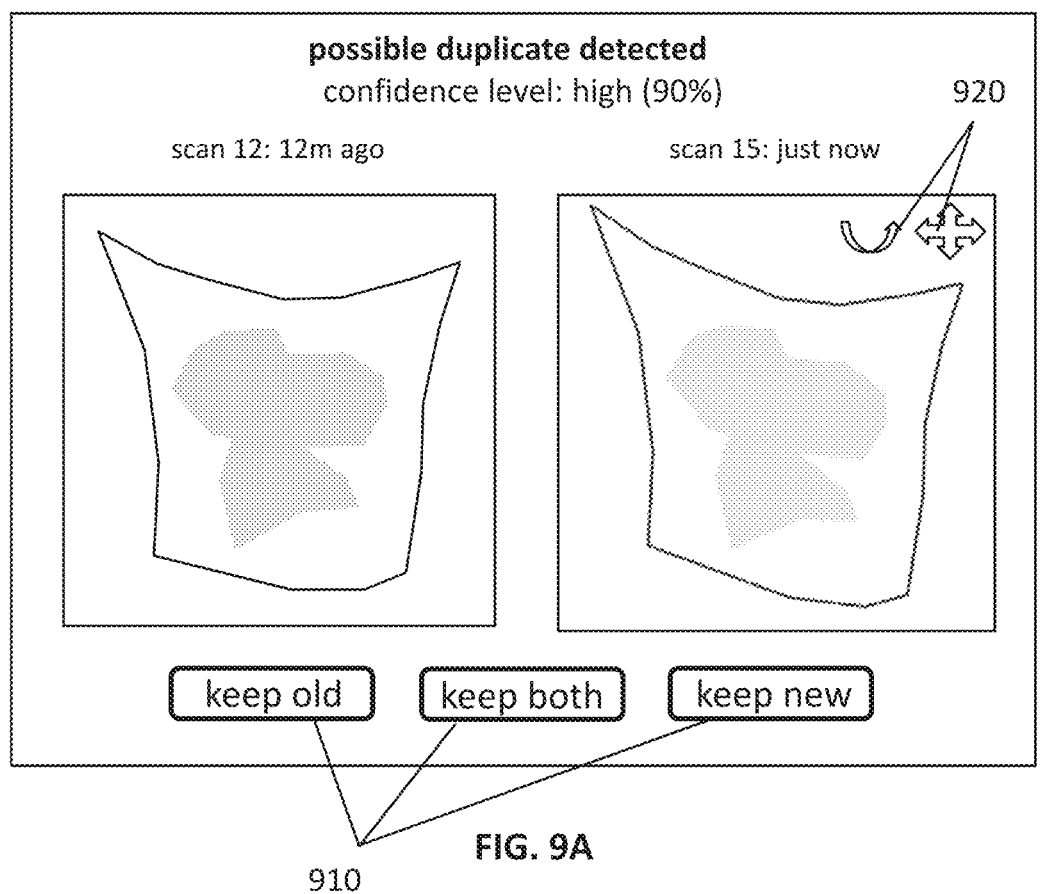
FIG. 9A is an exemplary display for communicating to a user regarding an image pair that potentially depicts the same surgical textile.

If a measure of duplicate likelihood meets a predetermined threshold (e.g., is determined to sufficiently indicate a potential duplicate image pair), then the method may include communicating the potential duplicity to a user. In some variations as shown in FIG. 9A, the communication may include a display notification visually presented to a user, indicating that a possible duplicate image has been obtained or received. The measure of duplicate likelihood or a representation thereof (e.g., presented as a confidence level) and/or the suspected duplicate image pair may be displayed. The user may be prompted to perform one or more actions in response to the detection of a possible duplicate image pair. For example, the user may be prompted to perform a manual count of surgical textiles that have been imaged up to that point, and asked to reconcile any discrepancies. As another example, the user may be prompted to use a user interface (e.g., touchscreen) to confirm whether the suspected duplicate image pair actually depicts the same textile (e.g., by reviewing the fluid patterns in the suspected duplicate image pair, remembering situational context of when the images were taken, weighing textiles depicted in suspected duplicate images to confirm distinctiveness based on different fluid weights, etc.). As another example, the user may be prompted to select one or both images in the suspected duplicate image pair for retention (e.g., with buttons 910) and/or deletion from the display and/or storage (and/or a decrement in an index counter, if the deleted image was previously associated with an increment to the index counter), thereby effectively removing the duplicity (and keeping textile count as accurate as possible). The method may, in some variations, include detecting one or more kinds of textile transformations between the image pair, such as rotation, flipping, or out-of-plane orientations, etc. and displaying the detected kinds of transformations, which may aid the user in verifying whether the images depict the same textile. Additionally or alternatively, the method may include adjusting at least one of the potential duplicate images to compensate for one or more kinds of textile transformations (e.g., rotating, flipping, deskewing, etc.) and displaying the adjusted images to be as similar in orientation as possible, which may aid the user in mentally resolving image differences and verifying whether the images depict the same textile. The image adjustments may be automatically performed based on what kind of textile transformation is detected, though additionally or alternatively the user may use an interface (e.g., with direction arrow buttons 920, etc.) to manually adjust the orientation of one or both images.

Figure 9B:
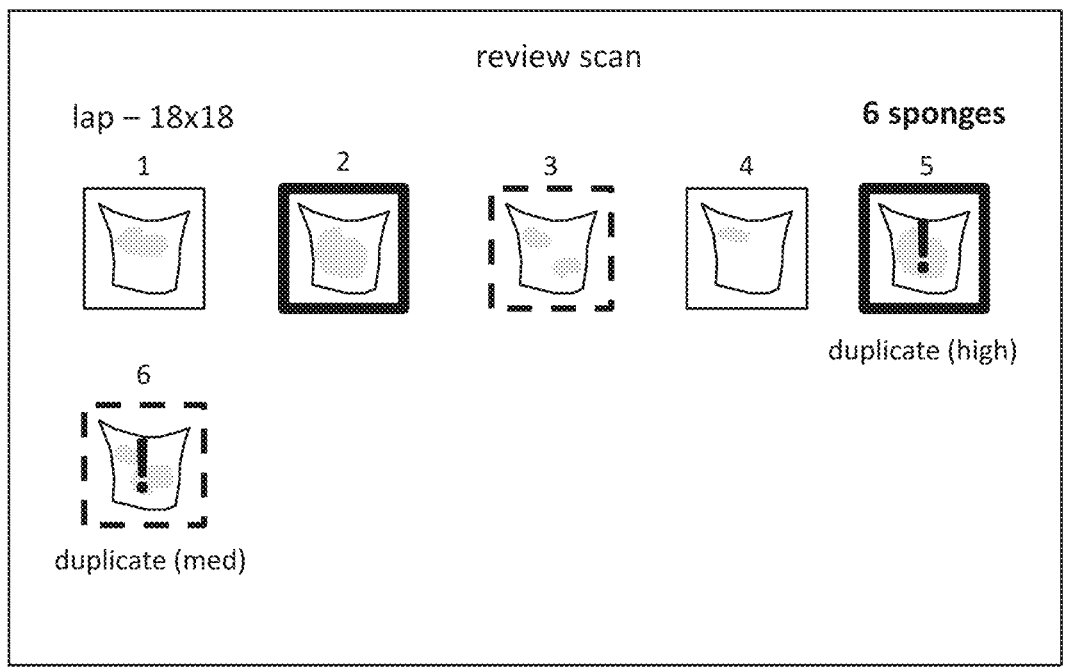
FIG. 9B is an exemplary display for displaying images of surgical textiles and communicating to a user regarding multiple image pairs, where each image pair potentially depicts the same surgical textile.

In some variations, as shown in FIG. 9B, communicating a potential duplicate image may include displaying some or all images obtained or received, and visually indicating potential groups of duplicates. For example, potential duplicate image pairs may be indicated with connecting lines (between images), and/or matching borders. Potential duplicate image pairs may be differentiated based on, for example, line weight, line patterns, color, etc. Other visual indications (e.g., color tinting, fading, etc.) may similarly be used to identify potential duplicate image pairs. Furthermore, measures of duplicate likelihood of the image pairs, or a representation thereof (e.g., presented as a confidence level) may be communicated with labels, by thickness of line weight, or other suitable manners. For example, as shown in FIG. 9B, images 2 and 5 have a high measure of duplicate likelihood, as indicated with heavy line weight and corresponding caption, while images 3 and 5 have a medium measure of duplicate likelihood, as indicated with a medium line weight and corresponding caption.

In yet other variations, communicating potential duplicate image pairs may include a displayed warning and/or an audible alarm warning such as a beep, tone, and/or spoken word command, which indicates that a possible duplicate image has been obtained or received. Additionally, the warning may be communicated through the electronic medical record system (EMR). An alarm may be triggered, for example, when one possible duplicate has been detected or when a threshold number of possible duplicates have been detected.

Potential duplicate image pairs may be communicated to a user substantially real-time as each new image is received (e.g., immediately after an image is received and analyzed to determine a measure of duplicate imaging relative to previously received images). For example, a user interlace may display a prompt similar to that shown in FIG. 9A soon after an image is obtained or received, if the new image is predicted to be a potential duplicate. Additionally or alternatively, potential duplicate image pairs may be communicated to a user in an image review pane, which may display at least some of the images in an overview screen. For example, an image overview screen may display all images obtained up to that point (e.g., during the surgical procedure, or at the end of the surgical procedure) and communicate all potential duplicate images on the overview screen. As another example, an image overview screen may be limited to displaying images depicting a selected type of textile (e.g., tap sponge) and communicating all potential duplicate images on the type-specific overview screen, similar to that shown in FIG. 9B. Potential duplicate images may be selected from the overview screen and confirmed as depicting the same textile (or not depicting the same textile), selected for retention, selected for deletion, etc. as described above.

As described above, the method may include conditionally modifying an index counter representing a textile count based on a comparison between the measure of duplicate likelihood and at least one predetermined threshold. For example, if the measure of duplicate likelihood does not meet a predetermined threshold (e.g., in the absence of detection of a potential duplicate image), then the method may include incrementing the index counter. In contrast, upon detection of a potential duplicate image of a surgical textile, the method may, for example, automatically withhold from incrementing a textile count index counter or decrement a previously-incremented index counter. Furthermore, in variations in which the measure of duplicate likelihood for a pair of images is compared to multiple thresholds, different consequences may result from the comparison to the different thresholds. For example, if the measure of duplicate likelihood does not meet a first threshold and therefore indicates a "low" risk of potential duplicates, then the method may include withholding from communicating any alert or warning to the user. If the measure of duplicate likelihood meets the first threshold but not a second threshold and therefore indicates a "medium" risk of potential duplicates, then the method may include communicating the risk of the potential duplicate image pair (e.g., requesting confirmation by the user whether the images depict the same textile) and accepting the user's conclusion of whether the images are duplicates. If the measure of duplicate likelihood meets the second threshold and therefore indicates a "high" risk of potential duplicates, then the method may include communicating the risk of the potential duplicate image pair but programmatically withhold from incrementing the textile count index counter, even if the user attempts to confirm that the images are not duplicates (or the method may require additional such confirmation, such as from multiple users providing confirmation in concurrence.

In some variations, the method may include generating an aggregate risk score for a set of received images (e.g., all images collected during a procedure, or a subset thereof), where the aggregate risk score incorporates the likelihood of duplicate imaging among some or all of the various images or image pairs in the set and generally indicates level of uncertainty in the overall textile count as contributed by potential duplicate images, for example, an aggregate risk score for an entire set of images (e.g., generally indicating level of uncertainty that the set includes at least one duplicate image) may be determined, such as by multiplying all measures of duplicate likelihood generated for each image pair in the set of images. As another example, an aggregate risk score for one selected image (e.g., generally indicating level of uncertainty that the selected image depicts the same textile as any other image in the set of images) may be determined, such as by multiplying all measures of duplicate likelihood generated for each image pair including the selected image. Similarly, an aggregate risk score of multiple selected images (e.g., generally indicating level of uncertainty that any of the selected images depict the same textile as any other image in the set of images) may be determined, such as by multiplying all measures of duplicate likelihood generated for each image pair including any of the selected images. As yet another example, an aggregate risk score for multiple images relative to one or more selected images (e.g., generally indicating level of uncertainty that any of the multiple images depict the same textile as any of the selected images) may be determined, such as by multiplying all measures of duplicate likelihood generated for each image pair between any of the multiple images and any of the selected images.

Similarly, the method may additionally or alternatively include generating a confidence level (or confidence percentage, score, etc.) that is generally an inverse of any of the aggregate risk score described above, where a confidence level generally indicates level of certainty that the overall textile count is accurate (e.g., level of certainty that there are no duplicate images).

Furthermore, the aggregate risk score and/or confidence level may be displayed on a display to the user, such as on an image overview screen as shown in FIG. 9O (e.g., presented as "duplicate risk score" or "confidence lever"). Additionally or alternatively, the aggregate risk score and/or confidence level may be communicated audibly via a speaker device. In some variations, an alarm (e.g., displayed and/or audible alarm) may be triggered when an aggregate risk score or confidence level satisfies a predetermined threshold (e.g., when an aggregate risk score for all images collected up to that point is above a predetermined threshold value, or when a confidence level is below a predetermined threshold value).

Figure 9C:
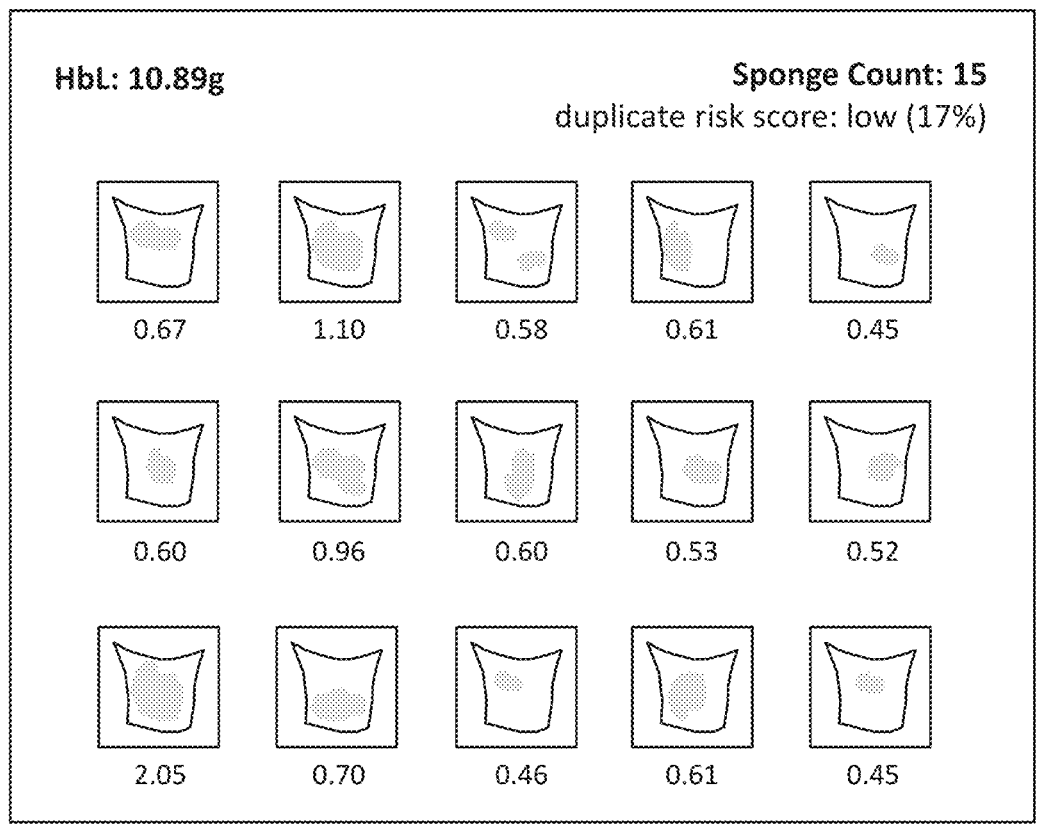
FIG. 9C is an exemplary display for displaying images of surgical textiles with a textile count and aggregate risk score of duplicate images.

Furthermore, the method may include displaying the index counter value for the surgical textile count, such as on an overview screen similar to that shown in FIG. 9C, or any suitable display. Additionally or alternatively, the method may include communicating the index counter value with an audible count, such as with a speaker device. In some variations, the surgical textile count may be stored in an electronic medical record for the patient, such as automatically upon conclusion of the surgical procedure (and/or intermittently as the surgical procedure proceeds) or upon user instruction on a user interface to add the surgical textile count to an electronic medical record.

Even further, the method may include displaying quantified aspects of the fluid contained in the surgical textiles, such as mass, volume, weight, concentration, etc. of the fluid or a fluid component contained in the surgical textiles, to help track extracorporeal fluid loss from a patient. For example, as shown in FIG. 9C, the method may include displaying estimated hemoglobin mass (e.g., determined as described above) in the surgical textile each image, and or an overall total of hemoglobin mass aggregated over the textiles depicted in all the images. In some variations, the quantified aspects of the fluid or fluid component in the surgical textiles (quantity for each textile and/or aggregated quantities) may be stored in an electronic medical record for the patient, such as automatically upon conclusion of the surgical procedure (and/or intermittently as the surgical procedure proceeds) or upon user instruction on a user interface to add the surgical textile count to an electronic medical record.

Uniformly Appearing Textiles

In some cases, uniformly appearing textiles may be difficult to visually differentiate from one another based on pattern recognition techniques described herein. Exemplary types of uniformly appearing textiles include unused textiles (e.g., clean), textiles that include only saline and/or other substantially transparent fluids, and fully saturated textiles (e.g., generally uniform shade of pink, red, etc. while saturated with blood). However, accuracy of a surgical textile count may result from an inability to distinguish between images of textiles having uniform appearances of the same general type. Accordingly, in some variations, the method may include one or more features for addressing potential duplicate imaging of uniformly appearing textiles.

In one variation, upon detecting that two or more images depict the same type of uniformly appearing textile, the method may include automatically classifying the images as potential duplicate images. For example, pattern recognition techniques described herein may detect that first and second textile-depicting images depict a "blank" textile (e.g., unused or includes a transparent fluid), which may result in a high measure of duplicate likelihood. In some variations, the user may be prompted and or permitted to confirm that the images are not duplicates. In some variations, the user may be prevented from confirming that the images are not duplicates, such that the uniformly appearing textiles automatically contribute to a higher risk score or lower confidence level as described above, regardless of whether the user attempts to confirm that the images depict distinct textiles.

In another variation, upon detecting that two or more images depict the same type of uniformly appearing textile, the method may include performing a secondary image processing technique for distinguishing between the images. For example, a classifying algorithm (similar to those discussed above) may classify an image or image region as depicting a surgical textile that is substantially uniformly saturated (e.g., substantially uniform shade of pink or red) or substantially uniformly unsaturated (e.g., substantially uniformly white). The classifying algorithm may, for example, use photometric and/or geometric methods for determining uniformity in appearance of the textile. If the classifying algorithm determines that the image depicts a surgical textile that is not uniformly appearing, then the method may include performing any one or more of the fluid pattern recognition techniques described above. On the other hand, if the classifying algorithm determines the image as depicting a uniformly appearing surgical textile, then the method may include performing an additional, secondary image processing technique. For example, the secondary image processing technique for distinguishing between two or more images depicting uniformly appearing textiles may include extracting a color-based feature (e.g., mean color component value such as RGB, CMYK, etc.) and/or a texture-based feature (e.g., contrast) from pixels or pixel groups in the images. Based on the similarity or dissimilarity of the extracted color-based features and/or texture-based features between the images, the images may be considered likely to be duplicate images or not likely to be duplicate images, respectively. Similarity or dissimilarity of the extracted color-based features and/or texture-based features may, for example, be measured by comparing extracted features from spatially-corresponding pixels or pixel groups between the images, histogram bin distributions of color component values, textile areas or si/e (e.g., based on number of pixels having a given color component value or range of values, or overall textile area), K-nearest neighbor algorithm, etc.

Furthermore, the method may, in some variations, additionally or alternatively include alerting or otherwise communicating to the user that two or more images are detected to depict the same type of uniformly appearing textile. For example, the method may include prompting the user to confirm whether the images are duplicates. If the images depict distinct textiles, the user may be prompted to tag or mark one or more of the textiles with a unique identifier (e.g., a colored or IR-detectable or UV-detectable dye to create a unique fluid pattern, label with a fabric marker, etc.) and re-image the tagged textile or textiles. For example, the new image of the tagged textiles may function to create a record supporting the confirmation that the imaged textiles were distinct.

In yet another variation, tracking blank textiles or other uniformly appearing textiles may be performed at least in part by generating an image that collectively depicts all the uniformly appearing textiles (e.g., laid out on a tray or other surface, hung against a wall or other background, or otherwise displayed such that each textile is separately visible in the image) and using computer vision techniques (e.g., edge detection, etc.) to identify each separate textile. Furthermore, the method may include incrementing an index counter as a textile counter based on the number of identified textiles in the image. Imaging all the uniformly appearing textiles collectively may, for example, confirm the existence and number of distinct, similarly-looking uniform textiles.

Other Variations

Other variations of the method for tracking surgical textiles may additionally or alternatively include other suitable computer vision and image classification techniques.

Image Warping Approach

Figure 11:
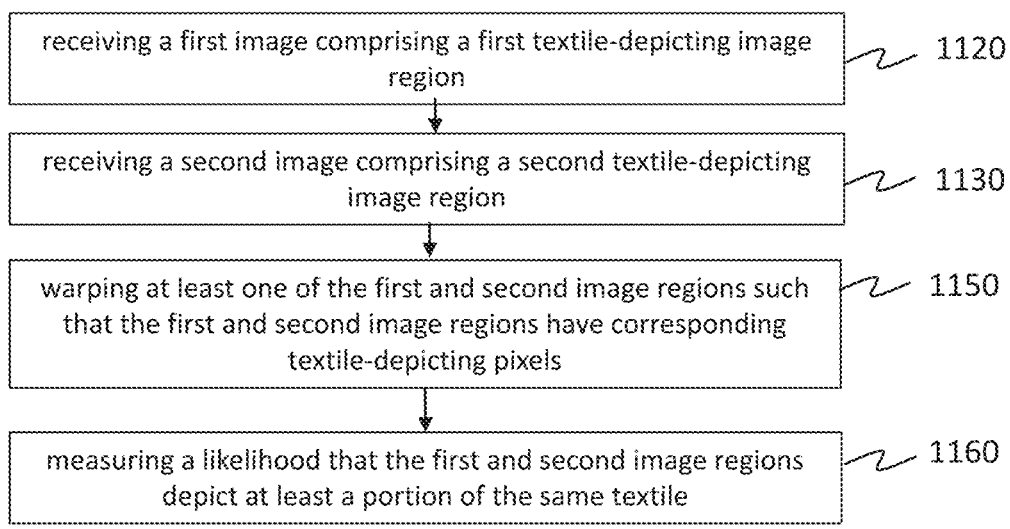
FIG. 11 is a flowchart schematic of another variation of a method for tracking surgical items.

In one variation, as shown in FIG. 11, the method may include receiving a first image comprising a first textile-depicting image region 1120, receiving a second image comprising a second textile-depicting image region 1130, warping at least one of the first and second image regions such that the first and second image regions have corresponding textile-depicting pixels (or pixel groups) 1150, and measuring a likelihood that the first and second image regions depict at least a portion of the same textile 1160. The measure of likelihood may, in some variations, be at least partially based on similarity of the corresponding textile-depicting pixels (or pixel groups).

For example, the corners of the textiles may be located and used to warp two or more images onto the same square or other suitable shape to facilitate image comparison (e.g., via a textile mask). There are various suitable ways to find the corners of a textile. For example, a gradient-based method such as the Harris corner detection algorithm may be used to generate guesses at candidate corners, and prior shape knowledge about the corners (e.g., knowledge that the corners are generally usually a known distance range apart from each other, and/or the corners tend to fit roughly to a square, rectangle, or trapezoid, etc. that has a certain range of parameter settings) could be used to filter out the unlikely guesses. Another exemplary technique to find corners would be to fit lines to the edges of the textile and take their intersection points as corners. Some prior information could be used to get good initial guesses at the edge locations, such as the fact that the textiles are usually roughly upright (e.g., have their planar surface perpendicular to the optical axis of the camera), and so the edge coordinate locations (e.g., in (x,y) space, etc.) may by indicated by peaks in the histograms of the spatial coordinates of the textile contour. Furthermore, the median and quartiles of the x and y coordinates (or locations in another suitable coordinate system) of the textile mask should correspond roughly to the center and outer quarters of the actual textile, even if the textile is somewhat misshapen. Linear regression to the textile contour coordinates may be used to refine the edge guesses, and/or a robust regression technique (e.g., RANSAC, Huber loss, or simply two or more rounds of linear regression where the second round ignores outliers from the first, etc.) may be used to make these edge fits mote insensitive to spurious contour points Additionally, higher-order regression may be used to enable a better lit to the textile edges, since textile edges are not always completely straight. Finally, midpoints or other partway points of the textile edges could be found and could be used to divide the textile into multiple quadrants or tiles, so that each of these tiles could be warped separately into a square shape or other suitable shape, so as to approximate the effects of uneven stretching of the textile.

As an alternative or in addition to the corner-warping method described above, the 3D shape of the textile may be used to warp the sponges. For example, a linear or non-linear surface may be fitted to the depth map or point cloud of the textile, and a transformation may be computed that transforms this surface into a flat plane that is parallel to the camera imaging plane and at a fixed location and distance. As another example, a convex or non-convex optimization approach may be used to find a series of rigid and/or non-rigid transformations that transform the textile depth map or point cloud into the desired shape. Ultimately, the computed transformation may be applied to the (x, y) coordinates of the color pixels of the textile images to warp them to the desired shape. Note that it is possible to control the complexity and scale of any of these transformations; for example, complex, small-scale transformations may be allowed to smooth out local, 3D textures, or alternatively only simple, large-scale transformations may be allowed so as to preserve those textures, which for example may be useful if 3D-texture-based descriptors are to be used.

Once the images have been warped onto the same general shape, the method may include comparing their contents in any one or more suitable manners to generate a similarity score. In some variations, the measure of duplicate likelihood may be equal to the similarity score (and evaluated and used similar to the manner described above), while in other variations the similarity score may be adjusted and/or combined with other features to generate the measure of duplicate likelihood. For example, the method may include directly comparing the images' pixels to each other and taking their RMSD or RMSE. As another example, use method may treat the two square images as vectors and take their cosine similarity score, either separately for each channel or after concatenating each channel together. This may, for example, help account for ambient lighting variation, since such lighting variation may scale the pixel intensities generally equally, so that the relative intensities are not impacted. As another example, blood segmentation masks could be compared instead of pixel color themselves, and/or the blood and textile segmentation masks could be used to denoise the images before comparison by replacing each non-blood pixel with the median of the textile pixel colors. The color or bloodiness of a pixel need not be the other thing that is compared—for example, dense HOG or SIFT descriptor maps (or any other descriptor maps described herein or other suitable descriptor maps) could be computed and compared (i.e., each pixel may have a HOG or SIFT descriptor associated with it). Such descriptor maps may be computed before or after the warping process described above.

Additionally or alternatively to comparing individual pixels, the method may include pooling together and comparing blocks of pixels. In some variations, comparison at multiple scales (e.g., individual blocks, blocks of different sizes) may make the algorithm less sensitive to warping errors, uneven stretching effects, blood spreading, and/or other causes of small misalignments between corresponding pixels, etc. Comparing blocks of pixels may include averaging the pixel colors within each block, taking their pixel color histogram (in which case the comparison metric could be a histogram-comparison metric such as histogram-intersection, Mahalanobis distance. Bhattacharyya distance. Earth Mover's Distance, etc.) and/or any other type of pooling. The pooling could be done multiple times and need not be done at the same block-size-ratio each time. Furthermore, the blocks may be square-shaped or any suitable shape (e.g., honeycomb-shaped) and they may or may not overlap.

As another variation for comparing images, the method may include defining an edit distance between the two warped textiles, where an edit consists of moving a pixel or changing its color. Each edit may be associated with a cost, and an edit distance between two textiles may be defined as the lowest possible cost of transforming one textile into the other.

In yet another variation for comparing images, a pair of images tinder analysis may be fed into a convolutional neural network that is trained to give a similarity score. Similarity scores may be collected as features to determine if the two images are duplicates of the same textile. The images may be warped (e.g., using the methods described above) before being fed into the neural network, or they may be left unwarped. Depth maps and/or textile masks may be fed into the neural network alongside the color images, and other information such as SIFT descriptors and corner locations may be fed in as well. The two images may be stacked by channel so that the neural network treats them as one image with twice as many channels, or two networks may process the images separately and then combine their outputs in the upper layers (i.e. a "Siamese network" structure). Any suitable type of deep learning network may be used, including a fully-connected network, deep belief network, generative adversarial network, restricted Boltzmann machine, convolutional network with gated inputs, or any other suitable type of deep learning method.

In order to account for the fact that a textile can be flipped and rotated through any of 8 possible permutations, the method may include applying each of these permutations when comparing the two warped images and only keep the permutation that results in the highest duplicate-likelihood score. Any other heuristic could be used to choose a favored permutation, such as ranking or otherwise based on one or more of the similarity scores derived as described herein. Furthermore, a second classification algorithm may be trained specifically for the purpose of choosing the correct permutation in the case of duplicates. In some variations, such a second classification algorithm may be separate from a first classification algorithm. Alternatively, in some variations, there may be some information-sharing between the multiple classification algorithms. For example, at least two classifications may be performed by a single convolutional neural network that has at least two outputs. One of these outputs may estimate the duplicate likelihood and another of these outputs may estimate or choose the permutation, such that learned information from one of these tasks can help inform the other task. In some variations, the method may also use similarity scores from multiple permutations to inform duplicate recognition. For example, instead of simply taking the similarity score from the highest-scoring permutation, the method may take the ratio between the highest and second-highest similarity scores among the permutations, the intuition being that a true duplicate should only score well under one permutation, and all other permutations should get low similarity scores.

In some variations, the method may combine one or more such warping-and-similarity-score techniques with the previously-described SIFT methods and global-feature based techniques. For example, the textile corners may be used to prune out spurious SIFT keypoint matches and/or guide the homography that is fitted to the matches, or conversely the matched SIFT key points may be used to enhance the accuracy of the corner guesses or more accurately model any uneven stretching of the textiles. As another example, the keypoint-matching method described above may be used, but the warping technique may be applied first before computing any descriptors so as to make the descriptors more robust to variations in the positioning and shape of the textile. Additionally or alternatively, the features from the SIFT and global-feature methods may be concatenated with the features from the warping-and-similarity-score methods in order to enable better duplicate detection.

Bag-of-Words Approach

In another variation, the method may implement a "bag-of-words" model which treats local image features as "vocabulary." For example, each image (or textile-depicting image region in the image) may be segmented into a suitable number of subregions (e.g., between 10 and 100, between 25 and 75, or any suitable number). Suitable subregions may be identified, for example, based on color patterns and/or geometric shapes, etc. in the fluid pattern on the depicted textile. One or more image features comprising the vocabulary may then be identified in each of the subregions. Suitable image features may include, for example SIFT features as described above (or alternatively, SURF features or other suitable features derived from a suitable extraction algorithm). Each image or image region may then be characterized by and represented by a "bag-of-words" vector of occurrence counts of the vocabulary of image features. Accordingly, potential duplicate images may be identified by comparing their "bag-of-words" vectors (e.g., directly, via hash functions for faster lookup, etc.).

Feature Histogram Approach

In another variation, the method may implement a histogram-based model. Each image (or textile-depicting image region) may be represented by a histogram, where each histogram bin represents a different possible aspect of the image. For example, in one variation, a feature extraction algorithm (e.g., SURF, SIFT, etc.) may be used to learn a K-mean cluster from training images, and each histogram bin may be a K-cluster with a respective K-center. Accordingly, each image or image region may be represented as a histogram with K-bins based on the closeness of its similarly extracted features (e.g., SURF, SIFT, etc.) to the K-centers of the bins. Absolute difference between the histograms may then be used to measure how similar or dissimilar, the depicted surgical textiles are, and therefore determine a measure of likelihood whether any given pair (or larger group) of images depict the same textile. As another example, each histogram bin may correspond to color component values for pixels in the textile-depicting image region for each image, such that each image or image region may be represented by a histogram reflecting color component value distribution in the depicted surgical textile.

Textile Bag Imaging Approach

In some variations, the method may include receiving and analyzing images that depict at least one surgical textile placed in a surgical textile counter bag or other compartmentalized holder (e.g., box, bins, etc.). The surgical textile counter bag may include pockets or other compartments, each configured to hold a designed number (e.g., one) of surgical textiles for counting. The pockets may include a transparent window through which the surgical textile, which may be rolled, wadded-up, or otherwise compacted in a known manner (e.g., wrapped using a predetermined technique), is visible. In some variations, the method may include receiving at least one image of the surgical textile counter bag (e.g., an image collectively depicting multiple pockets, or multiple images each depicting a respective pocket). In such variations, the method may include using computer vision techniques (e.g., blob detection algorithms) to determine whether a surgical textile is present in each pocket, and generating a textile count based on the number of surgical textiles present. For example, the method may include extracting a color-based feature (e.g., color component value such as RGB, CMYK, etc.) and/or a texture-based feature (e.g., contrast) from pixels or pixel groups depicting a pocket or surgical textile. The extracted color-based and or texture-based features may be compared to known features of a mathematically-compacted (e.g., rolled, wadded-up, etc.) surgical textile to determine whether a textile is present in a pocket. Upon detecting a surgical textile is present in a pocket of the textile counter bag, the method may include incrementing an index counter for a textile count. Furthermore, distinct counts of textiles, such as blank textiles (unused or saturated with transparent fluids) or fully saturated textiles, may be generated by comparing the extracted color-based and/or texture-based features to known features of mathematically-compacted blank or fully saturated textiles.

Furthermore, in some variations, the method may include performing a three-dimensional (3D) scan of the surgical textile counter bag with a 3D imaging system. For example, the method may include using an infrared (IR) depth-sensing camera to perform a 3D scan of the surgical counter bag and determine contours of the pocket and/or of one or more textiles present in the pocket. The method may include applying a classification algorithm (e.g., a suitable classification algorithm described above) to classify the pocket as including a particular number of textiles (e.g., zero, one, two, or more). The classification algorithm may, for example, base its classification on contour features of pockets known to include zero, one, two, or more surgical textiles. The method may include modifying (or not modifying an index counter) for a textile count and/or triggering an alarm to the user of potential inaccuracy in the textile count, based on the classification of the number of textiles in each pocket. For example, based on the 3D scan of lite surgical textile counter bag, the method may determine whether more than one textile is present in a pocket, and subsequently communicate to the user (e.g., by visual and/or audible alert) that the textile count may be inaccurate and prompt the user to perform a manual recount of textiles.

Computer Vision Transforms of Tagged Textiles

In some variations, at least some (but not necessarily all) of the surgical textiles may be prelabeled or pretagged with a unique identifier. For example, at least some of the surgical textiles may be lagged with a scannable optical bar code, QR code, or other machine-readable identifier. However, when such tagged surgical textiles are saturated with a dark fluid such as blood, the fluid may visually obscure the machine-readable identifier (e.g., makes it difficult for a scanner to distinguish between black and while features in the bar code, etc.) and hampers the ability to determine an accurate textile count through scanning. To address this, one variation of a method for tracking surgical textiles includes applying one or more computer vision transforms on an image of the machine-readable identifier on a surgical textile, which acts as a filter to facilitate reading of the machine-readable identifier. For example, the method may include transforming the textile-depicting image region based on a color-based feature (e.g., color component value such as RGB, CMYK, etc.) and/or a texture-based feature (e.g., contrast) which may make it easier to visualize the data in the fluid-saturated machine-readable identifier. The machine-readable identifier on each depicted surgical textile may then be read from the transformed image region, thereby facilitating tracking of surgical textiles (and/or detection of duplicate imaging, etc.) despite possible obscuring of the identifier with dark fluid.

As another example, at least some of the surgical textiles may be lagged with an IR and/or UV-detectable fluid or other identifier. The IR or UV-detectable fluid may, for example, be a biocompatible and inert fluid. The IR and/or UV-detectable fluid may be applied to the surgical textiles in a unique fluid pattern particular to each textile, in this example, the method may include extracting an IR-based and/or UV-based feature from the machine-readable identifier depicted in the image, which may make it easier to visualize the data in the fluid-saturated machine-readable identifier. The machine-readable identifier on each depicted surgical textile may then be read based on the extracted IR-based and/or UV-based feature, thereby facilitating tracking of surgical textiles (and/or detection of duplicate imaging, etc.) despite possible obscuring of the identifier with dark fluid.

System

As shown in FIG. 1, a system 100 for tracking surgical textiles may include at least one processor 152 and memory 154 having instructions stored therein. The processor 152 may execute the stored instructions such that it is configured to receive a first image comprising a first textile-depicting image region, receive a second image comprising a second textile-depicting image region, and measure a likelihood that the first and second image regions depict at least a portion of the same textile. In this variations, the measure of likelihood is at least partially based on a first aspect of the first image region and a second aspect of the second image region. In another variation, the processor may be configured to warp at least one of the first and second image regions such that the first and second image regions have corresponding textile-depicting pixels (or pixel groups), and the measure of likelihood may be at least partially based on similarity between the corresponding textile-depicting pixels (or pixel groups). The system may further include an index counter, and the index counter may be incremented if the measure of likelihood is below a predetermined threshold. For example, in measuring the likelihood that the first and second image regions depict at least a portion of the same textile, the processor 152 may be configured to define at least one classification feature at least partially based on at least one of the first aspect of the first image region and the second aspect of the second image region, where the measure of likelihood is at least partially based on the classification feature. Generally, the system 100 may, in some variations, be configured to substantially perform any one or more variations of the methods described in further detail herein.

As further shown in FIG. 1, the system 100 may include a camera 156 for obtaining one or more color images of the surgical textile, and/or a display 158 for displaying one or more of the images (and/or quantified aspects of the fluid in the surgical textiles, measures of likelihood that two or more images depict the same textile, prompts to the user to confirm whether duplicate imaging has occurred, etc.). In some variations, some or all of the system 100 may be in an integrated device and placed near the patient during the surgical procedure (e.g., in the operation room) to assess patient fluids that are contained in the surgical textiles, and/or to facilitate textile counting), for example, the system 100 may at least partially include a handheld or mobile electronic computing device 150 (e.g., that executes a native fluid analysis application program). Such a handheld or mobile device may for example, be a tablet computer, laptop computer, mobile smartphone, etc., which may include a camera, processor, and display. However, in other variations, some or all of the system components may be separated as discrete, interconnected devices. For example, the camera and or display may be located substantially near the patient during the surgical or medical procedure (e.g., in the operating room) while the processor may be located at a remote location (e.g., in the operating room separate from the camera and/or display, or outside the operating room), communicating with camera and display through a wired or wireless connection or other network.

Generally, one or more processors 152 may be configured to execute the instructions that are stored in memory 154 such that, when it executes the instructions, the processor 152 performs aspects of the methods described herein, the instructions may be executed by computer-executable components integrated with the application, applet, host, server, network, website, communication service, communication interface hardware, firmware, software elements of a user computer or mobile device, wristband, smartphone, or any suitable combination thereof. The instructions may be stored on memory or other computer-readable medium such as RAMs, ROMs, flash memory, EEPROMs, optical devices (e.g., CD or DVD), hard drives, floppy drives, or any suitable device.

The one or more processors 152 may be configured to perform the methods substantially as described herein. For example, the one or more processors may be configured to receive a first image comprising a first textile-depicting image region, receive a second image comprising a second textile-depicting image region, measure a likelihood that the first and second image regions depict at least a portion of the same textile where the measure of likelihood is at least partially based on a first aspect of the first image region and a second aspect of the second image region, and increment an index counter if the measure of likelihood meets a predetermined threshold indicating duplicates. In some variations, the processor 152 may be configured to define at least one classification feature at least partially based on at least one of the first aspect of the first image region and the second aspect of the second image region, and may be further configured to measure of the likelihood that the first and second image regions depict at least a portion of the same textile at least partially based on the classification feature.

As described above, the one or more processors 152 may be integrated in a handheld or mobile device 150. In other variations, the one or more processors 152 may be incorporated into a computing device or system such as a cloud-based computer system, a mainframe computer system, a grid-computer system, or other suitable computer system. Additionally or alternatively, the one or more processors may be incorporated into a remote server that receives images of surgical textiles, reconstructs and/or analyzes the images as described above, and transmits quantifications of one or more aspects of fluid in the surgical textiles, surgical textile counts, etc. to another computing device having a display for displaying such information to a user.

The system may further include a camera 156 that functions to generate one or more images of the surgical textile against a background during the surgical procedure, such as a set of one or more still images or as pan of a video feed. The camera 156 may include at least one optical image sensor (e.g., CCD, CMOS, etc.) that captures a color optical digital image with ted, green, and blue (RGB) color components for the pixels, and/or other suitable optical components. For example, the camera 156 may include a single image sensor paired with suitable corresponding optics and/or filters (e.g., color fitter arrays such as a Bayer pattern filter). As another example, the camera 156 may include multiple image sensors paired with suitable corresponding optics, such as at least one prism or diffractive surface to divide while light into separate color channels (e.g., RGB), each of which is detected by a respective image sensor. However, the camera 156 may include any suitable image sensors and other optics components to enable the camera 156 to generate images.

The camera may be configured to transmit images to the processor for analysis, and/or to a database that stores the images. As previously described, the camera may be integrated in the same device as one or more of the other components of the system 100, or the camera may be a separate component that communicates the image data to the other components.

The system may further include a display 158 that functions to display or otherwise communicate to a user (e.g., doctor, nurse) information that is generated by the system 100, including but not limited to patient information, images of surgical textiles, quantified metrics characterizing aspects of fluid in the surgical textiles, measures of likelihood of duplicate imaging of surgical textiles, an index counter value for a textile (or other item) count, warnings or prompts to the user indicating potential duplicate imaging of surgical textiles, etc. The display 158 may include a screen on a handheld or mobile device, a computer monitor, a television screen, a projector screen, or other suitable display.

In some variations, the display 158 may be configured to display a user interface that enables the user to interact with displayed information. For example, the user interface may enable the user to manipulate the images (e.g., zoom, crop, rotate, etc.) or manually define the image region depicting at least a portion of a surgical textile. As another example, the user interface may enable the user to select display options (e.g., font, color, language, etc.) and/or content (e.g., patient information, quantified metrics or other fluid-related information, alerts, etc.). As yet another example, the user interface may enable the user to select images for deletion due to depicting a duplicate surgical textile, or rotate flip, or otherwise manipulate images on the display. In these variations, the display may be user-interactive and include a resistive or capacitive touch screen that is responsive to skin, a stylet, or other user contact. In other variations, the display 158 may be user-interactive via a cursor controlled by a mouse, keyboard, or other input device.

Additionally or alternatively, the system may include a speaker or other suitable audio system that communicates quantified metrics or other fluid-related information, value for an index counter for surgical textiles (or other items), and/or warnings or prompts to the user. The display and/or the audio system may, for example, provide alerts upon one or more quantified estimations meeting a threshold (e.g., estimated quantity of fluids or certain fluid components aggregated over multiple surgical textiles exceeds a threshold), which may be useful to prompt certain actions in response, such as providing a blood transfusion. As another example, the display and/or audio system may provide alerts or prompts to the user upon a measure of likelihood that two or more images depict the same surgical textile, which may be useful to prompt the user to confirm whether duplicate imaging has occurred, re-assess location of counted and/or uncounted surgical textiles, etc.

As shown in FIG. 1, the display 158 may be integrated in the same device as one or more components of the system 100. Additionally or alternatively, the display 158 may include a standalone separate monitor, screen, or other suitable display.

EXAMPLE

A training dataset was developed to learn potentially suitable classification features and classification algorithms for tracking surgical textiles using pattern recognition in optical images. The training dataset included 600 images depicting the same surgical sponge but with various transformations (e.g., rotation, out-of-plane orientation changes, sponge flipping, etc.) and 600 images depicting different surgical sponges. SIFT feature descriptors were used to identify keypoints within the depicted surgical textiles in the training dataset images, and a K-nearest neighbor algorithm was used to identify correspondence between keypoints between pairs of depicted sponges. Using the extracted features and identified corresponding keypoints, a set of classification features were generated. The classification features included the classification features listed in FIG. 5, where the estimated fluid component for fluidEstimate was hemoglobin mass. The classification features were ted into four candidate classification algorithms for training: K-nearest neighbor classifier (KNN), support vector machine classifier (SVC), random forest classifier (RF), and extra tree classifier (ET) machine learning techniques.

The trained algorithms were tested using four subsets of data pulled from a testing dataset including 300 images depicting the same surgical sponge but with various transformations and 300 images depicting different surgical sponges. Results for the trained algorithms variously applied to Set 0, Set 1, Set 2, and Set 3 are shown in FIG. 10. With respect to Set 0, random forest classifiers (RF) generally resulted in a true positive rate (rate for correctly detecting duplicate sponge images) between about 80-82% and a false positive rate (rate for incorrectly detecting duplicate sponge images) of between about 17-19%, leading to an F-score (measuring accuracy of the classification algorithm) of between about 0.813-814. A trained K-nearest neighbor classifier (KNN) resulted in a true positive rate of about 84% and a false positive rate of about 25%, leading to an F-score of about 0.801. Other results for the various candidate classification algorithms for testing data sets Set 1, Set 2, and Set 3 are summarized in FIG. 10. Overall the best performance in detecting duplicate image pairs was given by the random forest (RF) classification algorithm with n_est=25 for Set 0.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A computer-implemented method for tracking surgical textiles, comprising:
   receiving a first image comprising a first textile-depicting image region;
   receiving a second image comprising a second textile-depicting image region;
   measuring a likelihood that the first and second image regions depict at least a portion of the same textile;
   incrementing an index counter without requiring user confirmation, based on the likelihood not meeting a predetermined first threshold;
   determining an image transformation between the first and second image regions;
   adjusting the second image region relative to the first image region based on the image transformation;
   displaying the first image region and the adjusted second image region on a display device,
   incrementing the index counter, after providing notification and receiving user confirmation that the first and second images do not represent the same textile, based on the likelihood exceeding the predetermined first threshold but not exceeding a predetermined second threshold; and
   not incrementing the index counter, despite receiving user input that the first and second images do not represent the same textile, based on the likelihood exceeding the predetermined second threshold.

2. The method of claim 1, further comprising:
   defining at least one classification feature at least partially based on at least one of a first aspect of the first image region and a second aspect of the second image region, wherein the likelihood is based at least in part on the classification feature, wherein the first aspect comprises a plurality of first keypoints characterizing the first image region and the second aspect comprises a plurality of second key points characterizing the second image region, and wherein each of the first and second keypoints is associated with a respective feature descriptor.

3. The method of claim 2, wherein defining at least one classification feature comprises fitting a homography transform relating the plurality of first keypoints and the plurality of second keypoints, and wherein the adjusting of the second image region relative to the first image region comprises applying the homography transform to one of the first image region or the second image region.

4. The method of claim 2 wherein at least one of the first and second aspects characterizes a fluid pattern.

5. The method of claim 1 wherein the image transformation flips the first image and the second image relative to each other.

6. The method of claim 1 wherein the image transformation rotates the first and second images relative to each other.

7. The method of claim 1 wherein the image transformation deskews the first and second images relative to each other.

8. The method of claim 1, further comprising:
receiving user input relating to whether or not the first image region and second image region depict the same textile; and
based on the user input, either changing or not changing a textile count.

9. The method of claim 1, further comprising:
incrementing the index counter despite the likelihood exceeding the predetermined second threshold after receiving additional user input confirming that the first and second images do not represent the same textile.

10. The method of claim 1, further comprising displaying the index counter on a display.

11. A computer system comprising:
one or more processors; and
a memory storing instructions that, when executed by the one or more processors, configure the computer system to performing operations comprising:
receiving a first image comprising a first textile-depicting image region;
receiving a second image comprising a second textile-depicting image region;
measuring a likelihood that the first and second image regions depict at least a portion of the same textile;
incrementing a textile count without requiring user confirmation, based on the likelihood not meeting a predetermined first threshold;
determining an image transformation between the first and second image regions;
adjusting the second image region relative to the first image region based on the image transformation;
displaying the first image region and the adjusted second image region on a display device;
incrementing the textile count, after providing notification and receiving user confirmation that the first and second images do not represent the same textile, based on the likelihood exceeding the predetermined first threshold but not exceeding a predetermined second threshold; and
not incrementing the textile count, despite receiving user input that the first and second images do not represent the same textile, based on the likelihood exceeding the predetermined second threshold.

12. The computer system of claim 11, wherein the operations further comprise:
defining at least one classification feature at least partially based on at least one of a first aspect of the first image region and a second aspect of the second image region, wherein the likelihood is based at least in part on the classification feature, wherein the first aspect comprises a plurality of first keypoints characterizing the first image region and the second aspect comprises a plurality of second key points characterizing the second image region, and wherein each of the first and second keypoints is associated with a respective feature descriptor.

13. The computer system of claim 12, wherein defining at least one classification feature comprises fitting a homography transform relating the plurality of first keypoints and the plurality of second keypoints, and wherein the adjusting of the second image region relative to the first image region comprises applying the homography transform to one of the first image region or the second image region.

14. The computer system of claim 12 wherein at least one of the first and second aspects characterizes a fluid pattern.

15. The computer system of claim 11, wherein the image transformation flips the first image and the second image relative to each other.

16. The computer system of claim 11, wherein the image transformation rotates the first and second images relative to each other.

17. The computer system of claim 11, wherein the image transformation deskews the first and second images relative to each other.

18. The computer system of claim 11, wherein the operations further comprise:
receiving user input relating to whether or not the first image region and second image region depict the same textile; and
based on the user input, either changing or not changing a textile count.

19. The computer system of claim 11, wherein the operations further comprise:
incrementing the textile count despite the likelihood exceeding the predetermined second threshold after receiving additional user input confirming that the first and second images do not represent the same textile.

20. A non-transitory computer-readable storage medium, the computer-readable storage medium including instructions that when executed by a computer system, cause the computer system to performing operations comprising:
receiving a first image comprising a first textile-depicting image region;
receiving a second image comprising a second textile-depicting image region;
measuring a likelihood that the first and second image regions depict at least a portion of the same textile;
incrementing a textile count without requiring user confirmation, based on the likelihood not meeting a predetermined first threshold;
determining an image transformation between the first and second image regions;
adjusting the second image region relative to the first image region based on the image transformation;
displaying the first image region and the adjusted second image region on a display device;
incrementing the textile count, after providing notification and receiving user confirmation that the first and second images do not represent the same textile, based on the likelihood exceeding the predetermined first threshold but not exceeding a predetermined second threshold; and
not incrementing the textile count, despite receiving user input that the first and second images do not represent the same textile, based on the likelihood exceeding the predetermined second threshold.

21. The computer-readable storage medium of claim 20, wherein the operations further comprise:

defining at least one classification feature at least partially based on at least one of a first aspect of the first image region and a second aspect of the second image region, wherein the likelihood is based at least in part on the classification feature, wherein the first aspect comprises a plurality of first keypoints characterizing the first image region and the second aspect comprises a plurality of second key points characterizing the second image region, and wherein each of the first and second keypoints is associated with a respective feature descriptor.

22. The computer-readable storage medium of claim 21, wherein defining at least one classification feature comprises fitting a homography transform relating the plurality of first keypoints and the plurality of second keypoints, and wherein the adjusting of the second image region relative to the first image region comprises applying the homography transform to one of the first image region or the second image region.

23. The computer-readable storage medium of claim 21 wherein at least one of the first and second aspects characterizes a fluid pattern.

24. The computer-readable storage medium of claim 20, wherein the image transformation flips the first image and the second image relative to each other.

25. The computer-readable storage medium of claim 20, wherein the image transformation rotates the first and second images relative to each other.

26. The computer-readable storage medium of claim 20, wherein the image transformation deskews the first and second images relative to each other.

27. The computer-readable storage medium of claim 20, wherein the operations further comprise:
    receiving user input relating to whether or not the first image region and second image region depict the same textile; and
    based on the user input, either changing or not changing a textile count.

28. The computer-readable storage medium of claim 20, wherein the operations further comprise:
    incrementing the textile count despite the likelihood exceeding the predetermined second threshold after receiving additional user input confirming that the first and second images do not represent the same textile.

\* \* \* \* \*

UNITED STATES PATENT AND TRADEMARK OFFICE
CERTIFICATE OF CORRECTION

PATENT NO. : 11,109,941 B2
APPLICATION NO. : 16/459418
DATED : September 7, 2021
INVENTOR(S) : Kumar et al.

It is certified that error appears in the above-identified patent and that said Letters Patent is hereby corrected as shown below:

In the Specification

In Column 1, Line 44, delete "stall" and insert --staff-- therefor

In Column 1, Line 60, delete "lagged" and insert --tagged-- therefor

In Column 2, Line 15, delete "of" and insert --if-- therefor

In Column 2, Lines 25-26, delete "and or" and insert --and/or-- therefor

In Column 2, Line 29, delete "pan" and insert --part-- therefor

In Column 2, Line 32, delete "mote" and insert --more-- therefor

In Column 3, Line 12, delete "and or" and insert --and/or-- therefor

In Column 3, Line 22, delete "use" and insert --the-- therefor

In Column 4, Line 1, delete "textile, in" and insert --textile. In-- therefor

In Column 4, Line 20, delete "mage" and insert --image-- therefor

In Column 5, Line 48, delete "and or" and insert --and/or-- therefor

In Column 5, Line 62, delete "and or" and insert --and/or-- therefor

In Column 6, Lines 23-24, delete "and or" and insert --and/or-- therefor

In Column 6, Line 55, delete "and or" and insert --and/or-- therefor

Signed and Sealed this
Twenty-third Day of November, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,109,941 B2

In Column 7, Line 65, delete "feast" and insert --least-- therefor

In Column 9, Line 56, delete "and or" and insert --and/or-- therefor

In Column 9, Line 67, delete "and or" and insert --and/or-- therefor

In Column 10, Line 69, delete "and or" and insert --and/or-- therefor

In Column 11, Line 3, delete "and or" and insert --and/or-- therefor

In Column 11, Line 33, delete "distanceFearures" and insert --distanceFeatures-- therefor In Column 14, Line 55, delete "and or" and insert --and/or-- therefor In Column 20, Line 11, delete "interlace" and insert --interface-- therefor In Column 20, Line 65, delete "concurrence." and insert --concurrence).-- therefor In Column 21, Line 40, delete "90" and insert --9C-- therefor In Column 22, Line 3, delete "and or" and insert --and/or-- therefor In Column 22, Line 36, delete "and or" and insert --and/or-- therefor In Column 23, Line 11, delete "si/e" and insert --size-- therefor In Column 27, Line 37, delete "and or" and insert --and/or-- therefor In Column 28, Line 9, delete "lagged" and insert --tagged-- therefor In Column 28, Line 33, delete "lagged" and insert --tagged-- therefor In Column 29, Line 33, delete "and or" and insert --and/or-- therefor In the Claims In Column 32, Line 43, in Claim 1, delete "device," and insert --device;-- therefor